(12) United States Patent
Chan et al.

(10) Patent No.: US 10,040,825 B2
(45) Date of Patent: Aug. 7, 2018

(54) SOLUBLE FORMS OF HENDRA AND NIPAH VIRUS F GLYCOPROTEIN AND USES THEREOF

(75) Inventors: Yee-peng Chan, Bethesda, MD (US); Christopher Broder, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 1773 days.

(21) Appl. No.: 12/808,930

(22) PCT Filed: Dec. 19, 2008

(86) PCT No.: PCT/US2008/087719
§ 371 (c)(1),
(2), (4) Date: May 12, 2011

(87) PCT Pub. No.: WO2009/117035
PCT Pub. Date: Sep. 24, 2009

(65) Prior Publication Data
US 2011/0223172 A1    Sep. 15, 2011

Related U.S. Application Data

(60) Provisional application No. 61/006,107, filed on Dec. 19, 2007.

(51) Int. Cl.
*C07K 14/005* (2006.01)
*A61K 39/12* (2006.01)
*C07K 16/10* (2006.01)
*A61K 39/00* (2006.01)

(52) U.S. Cl.
CPC ............ *C07K 14/005* (2013.01); *A61K 39/12* (2013.01); *C07K 16/1027* (2013.01); *A61K 2039/505* (2013.01); *A61K 2039/6031* (2013.01); *C12N 2760/18222* (2013.01); *C12N 2760/18234* (2013.01)

(58) Field of Classification Search
None
See application file for complete search history.

(56) References Cited

PUBLICATIONS

Bossart KN, Mungall BA, Crameri G, Wang LF, Eaton BT, Broder CC. Inhibition of Henipavirus fusion and infection by heptad-derived peptides of the Nipah virus fusion glycoprotein. Virol J. Jul. 18, 2005;2:57.*
Bossart KN et al. Receptor binding, fusion inhibition, and induction of cross-reactive neutralizing antibodies by a soluble G glycoprotein of Hendra virus. J Virol. Jun. 2005;79(11):6690-702.*
Hoyne PA et al. High affinity insulin binding by soluble insulin receptor extracellular domain fused to a leucine zipper. FEBS Lett. Aug. 11, 2000;479(1-2):15-8.*
Wang XL et al. Enhancement of humoral immunity to the hCG beta protein antigen by fusing a molecular adjuvant C3d3. J Reprod Immunol. Oct. 2004;63(2):97-110.*
Bossart KN et al. Inhibition of Henipavirus fusion and infection by heptad-derived peptides of the Nipah virus fusion glycoprotein. Virol J. Jul. 18, 2005;2:57.*
Bossart KN et al. .Receptor binding, fusion inhibition, and induction of cross-reactive neutralizing antibodies by a soluble G glycoprotein of Hendra virus. J Virol. Jun. 2005;79(11):6690-702.*
Weingartl HM et al. Recombinant nipah virus vaccines protect pigs against challenge. J Virol. Aug. 2006;80(16):7929-38.*
Hoyne et al. FEBS Lett. Aug. 11, 2000 ;479(1-2):15-8.*
GenBank: CAD92362.1, Apr. 15, 2005, http://www.ncbi.nlm.nih.gov/protein/40644716?report=genbank&log$=protalign&blast_rank=1&RID=G2GFMUSK01R.*
Weissenhorn et al. Atomic structure of the ectodomain from HIV-1 gp41. Nature. May 22, 1997;387(6631):426-30.*
Harbury et al. Crystal structure of an isoleucine-zipper trimer, Nature, 1994, 371: 80-83.*
Pager et al. A mature and fusogenic form of the Nipah virus fusion protein requires proteolytic processing by cathepsin L. Virology. Mar. 15, 2006;346(2):251-7. Epub Feb. 7, 2006.*
Protein precipitation. From Wikipedia, the free encyclopedia. https://en.wikipedia.org/wiki/Protein_precipitation.*

* cited by examiner

*Primary Examiner* — Nianxiang Zou
(74) *Attorney, Agent, or Firm* — Morgan, Lewis & Bockius LLP

(57) ABSTRACT

This invention relates to soluble forms of F glycoprotein from Hendra and Nipah virus and to compositions comprising soluble forms of F glycoprotein from Hendra and Nipah virus. This invention further relates to soluble oligomers of F glycoprotein from Hendra and Nipah virus. This invention also relates to nucleic acids encoding soluble forms of F glycoprotein from Hendra and Nipah virus. This invention also relates to diagnostic and therapeutic methods using the soluble forms of F glycoprotein from Hendra and Nipah virus. Further, this invention relates to antibodies, including neutralizing antibodies, and to vaccines for the prevention, diagnosis and treatment of infection by Hendra and Nipah viruses.

6 Claims, 9 Drawing Sheets

SEQUENCE LISTING

<160> NUMBER OF SEQ ID NOS: 12

<210> SEQ ID NO 1
<211> LENGTH: 1464
<212> TYPE: DNA
<213> ORGANISM: Hendra virus

<400> SEQUENCE: 1

| | | | | | |
|---|---|---|---|---|---|
| atggctacac | aagaggtcag | gctaaagtgt | ttgctctgtg | ggatcatagt | tctggttttg | 60 |
| tcattagaag | ggctagggat | actacattat | gagaaactta | gtaagatagg | gctggttaaa | 120 |
| ggtattacaa | gaaagtacaa | gattaagagt | aacccttttga | ccaaggatat | tgtgatcaaa | 180 |
| atgatcccta | atgtctcgaa | tgtctcaaag | tgcaccggga | ctgttatgga | gaattacaaa | 240 |
| agcagactca | cagggattct | ctcaccaatc | aaaggcgcca | tcgaactgta | caataataac | 300 |
| acgcatgacc | tagttggtga | tgtcaagctt | gcaggtgtgg | tgatggcagg | gattgcaatc | 360 |
| gggatagcta | ctgctgcaca | aatcacagca | ggtgttgcct | tatatgaggc | aatgaagaac | 420 |
| gcagacaata | tcaataaact | caagagcagc | atagagtcta | caaatgaggc | tgttgtcaaa | 480 |
| ttacaggaaa | cagctgagaa | acagtctac | gtccttactg | ctcttcaaga | ttacatcaac | 540 |
| actaaccttg | ttcctacaat | agatcaaatt | agctgcaagc | aaacagagct | cgcattagac | 600 |
| ttggcgttgt | ctaagtatct | gtctgatctg | ctctttgttt | tcggacctaa | cttacaggat | 660 |
| ccagtctcta | attccatgac | tatccaagca | atatctcaag | catttggggg | caattacgaa | 720 |
| accttactga | gaacgcttgg | ttacgcgacc | gaggacttcg | acggcctttt | agaaagtgat | 780 |
| agcataacag | gccagatagt | ctatgtagat | ctcagtagct | attacataat | agtaagggtg | 840 |
| tattttccca | tactaacaga | gatccaacag | gcttatgtgc | aggagttgct | tccagtgagt | 900 |
| tttaataacg | ataattcaga | tggatcagc | attgtcccga | atttcgtgct | gattaggaac | 960 |
| acgctgattt | caaatataga | agtcaagtac | tgcttaatca | ccaagaaaag | tgtgatttgt | 1020 |
| aatcaggact | atgctacacc | catgacggct | agcgtgagag | aatgcttgac | aggatccaca | 1080 |
| gataagtgcc | caagggagtt | agtagtctca | tcccatgttc | caagatttgc | cctctcagga | 1140 |
| ggagtcttgt | ttgcaaattg | tataagtgtg | acatgtcagt | gtcagactac | tgggagggca | 1200 |
| atatctcaat | caggggaaca | gacactactg | atgattgaca | atactacctg | cacaacagtt | 1260 |
| gttctaggaa | acataatcat | aagccttgga | aaatatttgg | gatcaataaa | ttacaattct | 1320 |
| gagagcattg | ctgttgggcc | accagtctat | acagacaaag | ttgatatctc | aagtcagata | 1380 |
| tctagtatga | atcaatcact | acaacaatct | aaggattaca | ttaaagaagc | tcaaaagatc | 1440 |
| ttggacactg | tgaatccgtc | gttg | | | | 1464 |

<210> SEQ ID NO 2
<211> LENGTH: 488
<212> TYPE: PRT
<213> ORGANISM: Hendra virus

<400> SEQUENCE: 2

Met Ala Thr Gln Glu Val Arg Leu Lys Cys Leu Leu Cys Gly Ile Ile
1               5                   10                  15

Val Leu Val Leu Ser Leu Glu Gly Leu Gly Ile Leu His Tyr Glu Lys
            20                  25                  30

Leu Ser Lys Ile Gly Leu Val Lys Gly Ile Thr Arg Lys Tyr Lys Ile
        35                  40                  45

Lys Ser Asn Pro Leu Thr Lys Asp Ile Val Ile Lys Met Ile Pro Asn
    50                  55                  60

```
Val Ser Asn Val Ser Lys Cys Thr Gly Thr Val Met Glu Asn Tyr Lys
 65                  70                  75                  80

Ser Arg Leu Thr Gly Ile Leu Ser Pro Ile Lys Gly Ala Ile Glu Leu
                 85                  90                  95

Tyr Asn Asn Asn Thr His Asp Leu Val Gly Asp Val Lys Leu Ala Gly
             100                 105                 110

Val Val Met Ala Gly Ile Ala Ile Gly Ile Ala Thr Ala Ala Gln Ile
             115                 120                 125

Thr Ala Gly Val Ala Leu Tyr Glu Ala Met Lys Asn Ala Asp Asn Ile
         130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                 165                 170                 175

Asp Tyr Ile Asn Thr Asn Leu Val Pro Thr Ile Asp Gln Ile Ser Cys
             180                 185                 190

Lys Gln Thr Glu Leu Ala Leu Asp Leu Ala Leu Ser Lys Tyr Leu Ser
         195                 200                 205

Asp Leu Leu Phe Val Phe Gly Pro Asn Leu Gln Asp Pro Val Ser Asn
210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Gly Leu
                 245                 250                 255

Leu Glu Ser Asp Ser Ile Thr Gly Gln Ile Val Tyr Val Asp Leu Ser
             260                 265                 270

Ser Tyr Tyr Ile Ile Val Arg Val Tyr Phe Pro Ile Leu Thr Glu Ile
         275                 280                 285

Gln Gln Ala Tyr Val Gln Glu Leu Leu Pro Val Ser Phe Asn Asn Asp
290                 295                 300

Asn Ser Glu Trp Ile Ser Ile Val Pro Asn Phe Val Leu Ile Arg Asn
305                 310                 315                 320

Thr Leu Ile Ser Asn Ile Glu Val Lys Tyr Cys Leu Ile Thr Lys Lys
                 325                 330                 335

Ser Val Ile Cys Asn Gln Asp Tyr Ala Thr Pro Met Thr Ala Ser Val
             340                 345                 350

Arg Glu Cys Leu Thr Gly Ser Thr Asp Lys Cys Pro Arg Glu Leu Val
         355                 360                 365

Val Ser Ser His Val Pro Arg Phe Ala Leu Ser Gly Gly Val Leu Phe
370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                 405                 410                 415

Cys Thr Thr Val Val Leu Gly Asn Ile Ile Ile Ser Leu Gly Lys Tyr
             420                 425                 430

Leu Gly Ser Ile Asn Tyr Asn Ser Glu Ser Ile Ala Val Gly Pro Pro
         435                 440                 445

Val Tyr Thr Asp Lys Val Asp Ile Ser Ser Gln Ile Ser Ser Met Asn
         450                 455                 460

Gln Ser Leu Gln Gln Ser Lys Asp Tyr Ile Lys Glu Ala Gln Lys Ile
465                 470                 475                 480
```

Leu Asp Thr Val Asn Pro Ser Leu
              485

<210> SEQ ID NO 3
<211> LENGTH: 1464
<212> TYPE: DNA
<213> ORGANISM: Nipah virus

<400> SEQUENCE: 3

| | | | | |
|---|---|---|---|---|
| atggtagtta tacttgacaa gagatgttat tgtaatcttt taatattgat tttgatgatc | 60 |
| tcggagtgta gtgttgggat tctacattat gagaaattga gtaaaattgg acttgtcaaa | 120 |
| ggagtaacaa gaaaatacaa gattaaaagc aatcctctca caaagacat tgttataaaa | 180 |
| atgattccga atgtgtcgga catgtctcag tgcacaggga gtgtcatgga aaattataaa | 240 |
| acacgattaa acgtatctt aacacctata aagggagcgt tagagatcta caaaacaac | 300 |
| actcatgacc ttgtcggtga tgtgagatta gccggagtta taatggcagg agttgctatt | 360 |
| gggattgcaa ccgcagctca aatcactgca ggcgtagcac tatatgaggc aatgaagaat | 420 |
| gctgacaaca tcaacaaact caaaagcagc attgaatcaa ctaatgaagc tgtcgttaaa | 480 |
| cttcaagaga ctgcagaaaa acagtctat gtgctgactg ctctacagga ttacattaat | 540 |
| actaatttag taccgacaat tgacaagata agctgcaaac agacagaact ctcactagat | 600 |
| ctggcattat caaagtacct ctctgatttg cttttgtat ttggcccaa ccttcaagac | 660 |
| ccagttcta attcaatgac tatacaggct atatctcagg cattcggtgg aaattatgaa | 720 |
| acactgctaa gaacattggg ttacgctaca gaagacttg atgatcttct agaaagtgac | 780 |
| agcataacag gtcaaatcat ctatgttgat ctaagtagct actatataat tgtcagggtt | 840 |
| tattttccta ttctgactga aattcaacag gcctatatcc aagagttgtt accagtgagc | 900 |
| ttcaacaatg atgattcaga atggatcagt attgtcccaa atttcatatt ggtaaggaat | 960 |
| acattaatat caaatataga gattggattt tgcctaatta caagaggag cgtgatctgc | 1020 |
| aaccaagatt atgccacacc tatgaccaac aacatgagag aatgtttaac gggatcgact | 1080 |
| gagaagtgtc ctcgagagct ggttgtttca tcacatgttc ccagatttgc actatctaac | 1140 |
| ggggttctgt ttgccaattg cataagtgtt acatgtcagt gtcaaacaac aggcagggca | 1200 |
| atctcacaat caggagaaca aactctgctg atgattgaca acaccacctg tcctacagcc | 1260 |
| gtactcggta atgtgattat cagcttaggg aaatatctgg ggtcagtaaa ttataattct | 1320 |
| gaaggcattg ctatcggtcc tccagtcttt acagataaag ttgatatatc aagtcagata | 1380 |
| tccagcatga atcagtcctt acaacagtct aaggactata tcaaagaggc tcaacgactc | 1440 |
| cttgatactg ttaatccatc atta | 1464 |

<210> SEQ ID NO 4
<211> LENGTH: 488
<212> TYPE: PRT
<213> ORGANISM: Nipah virus

<400> SEQUENCE: 4

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn

```
                50              55              60
Val Ser Asp Met Ser Gln Cys Thr Gly Ser Val Met Glu Asn Tyr Lys
 65              70              75              80

Thr Arg Leu Asn Gly Ile Leu Thr Pro Ile Lys Gly Ala Leu Glu Ile
                 85              90              95

Tyr Lys Asn Asn Thr His Asp Leu Val Gly Asp Val Arg Leu Ala Gly
                100             105             110

Val Ile Met Ala Gly Val Ala Ile Gly Ile Ala Thr Ala Ala Gln Ile
            115             120             125

Thr Ala Gly Val Ala Leu Tyr Glu Ala Met Lys Asn Ala Asp Asn Ile
    130             135             140

Asn Lys Leu Lys Ser Ser Ile Glu Ser Thr Asn Glu Ala Val Val Lys
145             150             155             160

Leu Gln Glu Thr Ala Glu Lys Thr Val Tyr Val Leu Thr Ala Leu Gln
                165             170             175

Asp Tyr Ile Asn Thr Asn Leu Val Pro Thr Ile Asp Lys Ile Ser Cys
            180             185             190

Lys Gln Thr Glu Leu Ser Leu Asp Leu Ala Leu Ser Lys Tyr Leu Ser
            195             200             205

Asp Leu Leu Phe Val Phe Gly Pro Asn Leu Gln Asp Pro Val Ser Asn
    210             215             220

Ser Met Thr Ile Gln Ala Ile Ser Gln Ala Phe Gly Gly Asn Tyr Glu
225             230             235             240

Thr Leu Leu Arg Thr Leu Gly Tyr Ala Thr Glu Asp Phe Asp Asp Leu
                245             250             255

Leu Glu Ser Asp Ser Ile Thr Gly Gln Ile Ile Tyr Val Asp Leu Ser
            260             265             270

Ser Tyr Tyr Ile Ile Val Arg Val Tyr Phe Pro Ile Leu Thr Glu Ile
            275             280             285

Gln Gln Ala Tyr Ile Gln Glu Leu Leu Pro Val Ser Phe Asn Asn Asp
    290             295             300

Asp Ser Glu Trp Ile Ser Ile Val Pro Asn Phe Ile Leu Val Arg Asn
305             310             315             320

Thr Leu Ile Ser Asn Ile Glu Ile Gly Phe Cys Leu Ile Thr Lys Arg
                325             330             335

Ser Val Ile Cys Asn Gln Asp Tyr Ala Thr Pro Met Thr Asn Asn Met
            340             345             350

Arg Glu Cys Leu Thr Gly Ser Thr Glu Lys Cys Pro Arg Glu Leu Val
            355             360             365

Val Ser Ser His Val Pro Arg Phe Ala Leu Ser Asn Gly Val Leu Phe
    370             375             380

Ala Asn Cys Ile Ser Val Thr Cys Gln Cys Gln Thr Thr Gly Arg Ala
385             390             395             400

Ile Ser Gln Ser Gly Glu Gln Thr Leu Leu Met Ile Asp Asn Thr Thr
                405             410             415

Cys Pro Thr Ala Val Leu Gly Asn Val Ile Ile Ser Leu Gly Lys Tyr
            420             425             430

Leu Gly Ser Val Asn Tyr Asn Ser Glu Gly Ile Ala Ile Gly Pro Pro
            435             440             445

Val Phe Thr Asp Lys Val Asp Ile Ser Ser Gln Ile Ser Ser Met Asn
    450             455             460

Gln Ser Leu Gln Gln Ser Lys Asp Tyr Ile Lys Glu Ala Gln Arg Leu
465             470             475             480
```

Leu Asp Thr Val Asn Pro Ser Leu
            485

<210> SEQ ID NO 5
<211> LENGTH: 48
<212> TYPE: DNA
<213> ORGANISM: Artificial
<220> FEATURE:
<223> OTHER INFORMATION: Nucleotide sequence for S-peptide

<400> SEQUENCE: 5
aaggagaccg ctgctgctaa gttcgaacgc cagcacatgg attcttga                48

<210> SEQ ID NO 6
<211> LENGTH: 15
<212> TYPE: PRT
<213> ORGANISM: Artificial
<220> FEATURE:
<223> OTHER INFORMATION: Amino acid sequence for S-peptide

<400> SEQUENCE: 6

Lys Glu Thr Ala Ala Ala Lys Phe Glu Arg Gln His Met Asp Ser
1               5                   10                  15

<210> SEQ ID NO 7
<211> LENGTH: 117
<212> TYPE: DNA
<213> ORGANISM: Artificial
<220> FEATURE:
<223> OTHER INFORMATION: Nucleotide sequence for GPI

<400> SEQUENCE: 7
atcgatccaa ataaaggaag tggaaccact tcaggtacta cccgtcttct atctgggcac    60
acgtgtttca cgttgacagg tttgcttggg acgctagtaa ccatgggctt gctgact     117

<210> SEQ ID NO 8
<211> LENGTH: 39
<212> TYPE: PRT
<213> ORGANISM: Artificial
<220> FEATURE:
<223> OTHER INFORMATION: Amino acid sequence for GPI

<400> SEQUENCE: 8

Ile Asp Pro Asn Lys Gly Ser Gly Thr Thr Ser Gly Thr Thr Arg Leu
1               5                   10                  15

Leu Ser Gly His Thr Cys Phe Thr Leu Thr Gly Leu Leu Gly Thr Leu
                20                  25                  30

Val Thr Met Gly Leu Leu Thr
        35

<210> SEQ ID NO 9
<211> LENGTH: 93
<212> TYPE: DNA
<213> ORGANISM: Artificial
<220> FEATURE:
<223> OTHER INFORMATION: Nucleotide sequence for GCN4

<400> SEQUENCE: 9
atgaagcaga tcgaggacaa gatcgaggag atcctgagca agatctacca catcgagaac    60
gagatcgcca ggatcaagaa gctgatcggc gag                                93

<210> SEQ ID NO 10
<211> LENGTH: 31

```
<212> TYPE: PRT
<213> ORGANISM: Artificial
<220> FEATURE:
<223> OTHER INFORMATION: Amino acid sequence for GCN4

<400> SEQUENCE: 10

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu
            20                  25                  30

<210> SEQ ID NO 11
<211> LENGTH: 12
<212> TYPE: DNA
<213> ORGANISM: Artificial
<220> FEATURE:
<223> OTHER INFORMATION: Nucleotide sequence for Factor Xa

<400> SEQUENCE: 11
atcgagggca gg                                                             12

<210> SEQ ID NO 12
<211> LENGTH: 4
<212> TYPE: PRT
<213> ORGANISM: Artificial
<220> FEATURE:
<223> OTHER INFORMATION: Amino acid sequence for Factor Xa

<400> SEQUENCE: 12

Ile Glu Gly Arg
1
```

SOLUBLE FORMS OF HENDRA AND NIPAH VIRUS F GLYCOPROTEIN AND USES THEREOF

RELATED APPLICATIONS

The present application is a U.S. National Phase Application of International Application No. PCT/US2008/087719 (filed Dec. 19, 2008) which claims priority to U.S. Provisional Application No. 61/006,107 (filed Dec. 19, 2007) both of which are hereby incorporated by reference in their entirety.

ACKNOWLEDGEMENT OF FEDERAL SUPPORT

The present invention arose in part from research funded by the following federal grants: U54 AI057168 and R21 AI065597. The government may have certain rights to the invention.

SEQUENCE LISTING

A computer readable text file, entitled "044508-5020-SequenceListing.txt," created on or about Jun. 17, 2010 with a file size of about 14 kb contains the sequence listing for this application and is hereby incorporated by reference in its entirety.

FIELD OF THE INVENTION

The present invention relates to soluble forms of F glycoprotein from Hendra and Nipah viruses, to compositions comprising soluble forms of F glycoprotein from Hendra and Nipah virus, to antibodies reactive against soluble forms of F glycoprotein from Hendra and Nipah virus, and to methods related thereto.

BACKGROUND OF THE INVENTION

Nipah virus (NiV) and Hendra virus (HeV) are newly emergent zoonotic viruses that currently comprise their own genus, *Henipavirus*, within the family Paramyxoviridae. Paramyxoviruses are negative-sense RNA enveloped viruses and encompass a variety of important human and animal pathogens, including measles virus, mumps virus, Sendai virus, Newcastle disease virus, rinderpest virus, canine distemper virus, human parainfluenza viruses, respiratory syncytial virus, and simian virus 5 (reviewed in Lamb and Parks (2007) Fields Virology, eds. Knippe & Howley, Lippincott, Williams & Wilkins, pp. 1449-1496) The broad species tropisms of the Henipaviruses and the ability to cause fatal disease in both animals and humans distinguish HeV and NiV from all other known paramyxoviruses (reviewed in Eaton (2001) Microbes Infect 3:277-278). HeV and NiV are both regarded as Biological Safety Level-4 (BSL-4) pathogens, and are on the NIAID Biodefense research agenda as zoonotic emerging category C priority pathogens that could potentially be used as agents for bio-terrorism. Henipaviruses can be readily amplified in host livestock and can further cause disease in large animals. Henipaviruses can be aerosol transmitted to humans where disease may manifest as severe respiratory illness and febrile encephalitis. Human to human transmission is also possible. Henipaviruses can be readily grown in either cell culture or embryonated chicken eggs, can be produced in high un-concentrated titers (~$10^8$ TCID$_{50}$/ml), and can be highly infectious (Crameri et al. (2002) J. Virol. Methods 99:41-51; Field et al. (2001) Microbes Infect. 3:307-314; Hooper et al. (2001) Microbes Infect 3:315-322).

The principal reservoirs for both NiV and HeV appear to be several species of pteroid fruit bats, common to Southeast Asia and the Pacific, and hence most reported viral outbreaks seen to date have been in those areas (Eaton et al. (2006) Nat. Rev. Microbiol. 4:23-35). HeV first appeared in Australia in 1994 in two unrelated but similarly timed episodes of severe respiratory disease in horses, in which a total of three transmissions to humans were observed, two of which resulted in death. HeV reemerged through fatal equine infections in Australia in 1999, 2004, and 2006 (Field et al. (2000) Aust. Vet J. 78:279-280; Anonymous (2004) Int. Soc. for Infect. Dis. 20041214.3307; Murray (2006) World Org. for Animal Health Vol. 19-No. 26). NiV emerged in between 1997 and 1998 in an outbreak of encephalitis among pig farmers in both Malaysia and Singapore, generating 265 reports of human infection, of which 105 were fatal (Chua (2003) J. Clin. Virol. 26:265-275). NiV recently reemerged in Bangladesh. Two outbreaks of NiV occurred in 2004, and yet another in January of 2005 (Communicable Disease Report Weekly (2005) Vol. 15 No. 16). Several important observations in the more recent outbreaks have been made, including higher incidence of acute respiratory distress syndrome, person-to-person transmission, and significantly higher case fatality rates (approaching 75%) (Health and Science Bulletin (2004) 2:5-11; Hsu et al. (2004) Emerg. Infect. Dis. 10:2082-2087).

Physiologically, paramyxoviruses possess two major membrane-anchored glycoproteins in the envelope of the viral particle that are required for infection of a receptive host cell. The two glycoproteins serve different but complementary functions. One glycoprotein acts to achieve physical attachment with the host while the other glycoprotein acts to achieve effective fusion with the host. Typically, without the concerted action of both, the host cannot be infected.

The attachment glycoprotein is a type II membrane protein where the amino (N-) terminus is oriented toward the cytoplasm and the carboxy (C-) terminus is on the other side of the plasma membrane and in the extracellular material. The attachment glycoprotein can be either a hemagglutinin-neuraminidase protein (FIN), a hemagglutinin protein (H), or a glycoprotein (G) (which lacks hemagglutination and neuraminidase activities) depending on the particular virus (reviewed in Lamb & Parks (2007) Fields Virology, eds. Knippe & Howley, Lippincott Williams & Wilkins, pp. 1449-1496). Traditionally, the HN, H, and G proteins are the principal antigens to which virtually all neutralizing antibodies are directed. NiV and HeV both express G glycoproteins. Previous studies focusing on the G glycoproteins from NiV and HeV have yielded effective subunit vaccines and diagnostic reagents. The primary function of the paramyxovirus attachment glycoprotein is to engage appropriate receptors on the surfaces of host cells, which for the majority of well-characterized paramyxoviruses, are sialic acid moieties. HeV and NiV glycoprotein, however, utilizes the host cell protein receptors ephrinB2 and/or ephrinB3 (Bishop et al. (2007) J. Virol. 81:5893-5901; Bonaparte et al. (2005) Proc. Natl. Acad. Sci. U.S.A. 102: 10652-10657; Negrete et al. (2006) PLoS Pathog 2: e7).

The fusion (F) glycoprotein in paramyxoviruses mediates pH-independent membrane fusion between the virus and its host cell, which results in delivery of the nucleocapsid. Paramyxovirus F glycoproteins are trimeric class I fusogenic envelope glycoproteins, with the protein's N-terminus being located in the extracellular domain. An important feature of paramyxovirus F glycoproteins is the presence of two heptad repeat regions and a hydrophobic fusion peptide. HeV and NiV infect through a pH-independent membrane fusion process into the host cell by the concerted action of the attachment and fusion glycoproteins. In nearly all cases, both glycoproteins are required for efficient membrane fusion (Bossart & Broder (2007) Viral Entry into Host Cells, eds. Pohlmann & Simmons, Landes Bioscience).

Upon activation of the fusion mechanism, F glycoproteins will undergo conformational changes that facilitate the insertion of the fusion peptide into target membranes. The conformational changes bring the two heptad repeat regions together for the formation of a six-helix bundle structure (also called a trimer-of-hairpins). These conformational changes occur during or immediately following virus-cell membrane fusion (reviewed in Lamb et al. (2006) Virology 344:30-37). Several molecular details of the substantial conformational change of F glycoprotein have been revealed in the recent structural solutions of both post- and pre-fusion conformations of F glycoprotein (Yin et al. (2005) Proc. Natl. Acad. Sci. U.S.A. 102:9288-9293; Yin et al. (2006) Nature 439:38-44).

Research in Henipaviruses is of extreme importance for at least two major reasons: to gain insight into the physiology of these viruses, and to develop strategies to treat, to detect and to prevent their further outbreak. Currently, therapeutics and methodologies for diagnosis for NiV- or HeV-infected individuals are limited. Given the novelty and threat posed by these viruses, there is a need for improved means of treating and/or preventing an infection by NiV or HeV, as well as a means for accurately detecting an infection.

SUMMARY OF THE INVENTION

The present invention provides new tools and methods for the design, production and use of soluble forms of the F glycoprotein of Hendra virus and Nipah virus. The present invention relates to various soluble forms of the F glycoprotein from the Hendra or Nipah virus. The invention provides a non-membrane bound form of F glycoprotein from the Hendra and Nipah viruses. The invention provides for a soluble F glycoprotein suitable as an antigen for vaccination purposes. The invention further provides soluble forms of F glycoprotein suitable to identify and isolate antibodies that specifically bind to it. The invention further provides diagnostic kits comprising soluble forms of F glycoprotein suitable for detecting the presence of Hendra and Nipah viruses.

In one embodiment, the invention provides methods of producing soluble F glycoprotein derived from Hendra virus and/or Nipah virus. In some embodiments, the soluble F glycoprotein is produced by recombinant means. By way of example, the soluble F glycoprotein can be produced by genetic engineering. In other embodiments, the soluble F glycoprotein is produced as a synthetic polypeptide.

In another embodiment, the invention provides nucleic acid and polypeptide sequences or fragments, analogs or homologs thereof that encode a soluble F glycoprotein derived from Hendra or Nipah virus.

The invention also provides expression vectors comprising e nucleic ac d encoding a soluble F glycoprotein derived from Hendra and/or Nipah virus.

The invention also provides a fusion protein comprising a polypeptide of the invention and one or more additional polypeptides that enhance the stability of the present invention enhance the immunogenicity of the present invention and/or assist in the purification of the present invention. Other embodiments provide nucleic acids that encode the fusion proteins. Some embodiments provide soluble oligomers of F glycoprotein from Hendra and/or Nipah virus.

Another embodiment of the present invention provides antibodies and fragments thereof, such as neutralizing, humanized, monoclonal, chimeric and polyclonal antibodies, specific for a soluble F glycoprotein derived from Hendra and/or Nipah virus and diagnostic and/or therapeutic application of such antibodies.

Another embodiment provides subunit vaccine comprising the nucleotide or amino acid sequences of the invention.

Another embodiment of the invention provides methods of preventing infection by Hendra and/or Nipah virus in a subject or of mitigating an infection of Hendra and/or Nipah virus in a subject.

Another embodiment of this invention provides diagnostic kits comprising the nucleic acids, polypeptides and/or antibodies of the invention.

Other embodiments and advantages of the invention are set forth in part in the description, which follows, and in part, may be obvious from this description, or may be learned from the practice of the invention.

BRIEF DESCRIPTION OF THE DRAWINGS

FIG. 2 shows size exclusion chromatography analysis of NiV sF glycoprotein generated after Phospholipase D cleavage of a carboxy-terminus GPI sequence. FIG. 2A shows 300 μg of NiV sF glycoprotein-GPI analyzed on a calibrated Superdex™ 200 10/300 gel filtration column 400 μL fractions were then collected. The elution volume of each peak was used to determine the approximate molecular mass as depicted from the calibrated curve. Vo represents the void volume. FIG. 2B shows 5 μL of each fraction after analysis by Blue Native polyacrylamide gel electrophoresis (BN-PAGE) followed by western blotting. Immuno-detection was done by using a horseradish peroxidase (HRP) conjugated anti S-peptide antibody.

FIG. 3 shows size exclusion chromatography analysis of HeV sF glycoprotein with a carboxy terminal GCN peptide motif.

FIG. 4 shows size exclusion chromatography analysis of NiV sF glycoprotein with a carboxyl terminal GCN peptide motif

FIG. 5A shows a western blot of approximately 2 µg of protein loaded per lane. Immunodetection was done by using HRP conjugated anti S-peptide antibody. FIG. 5B shows Coomassie Blue staining of approximately 5 µg of protein loaded per lane.

DETAILED DESCRIPTION

Figure 1:
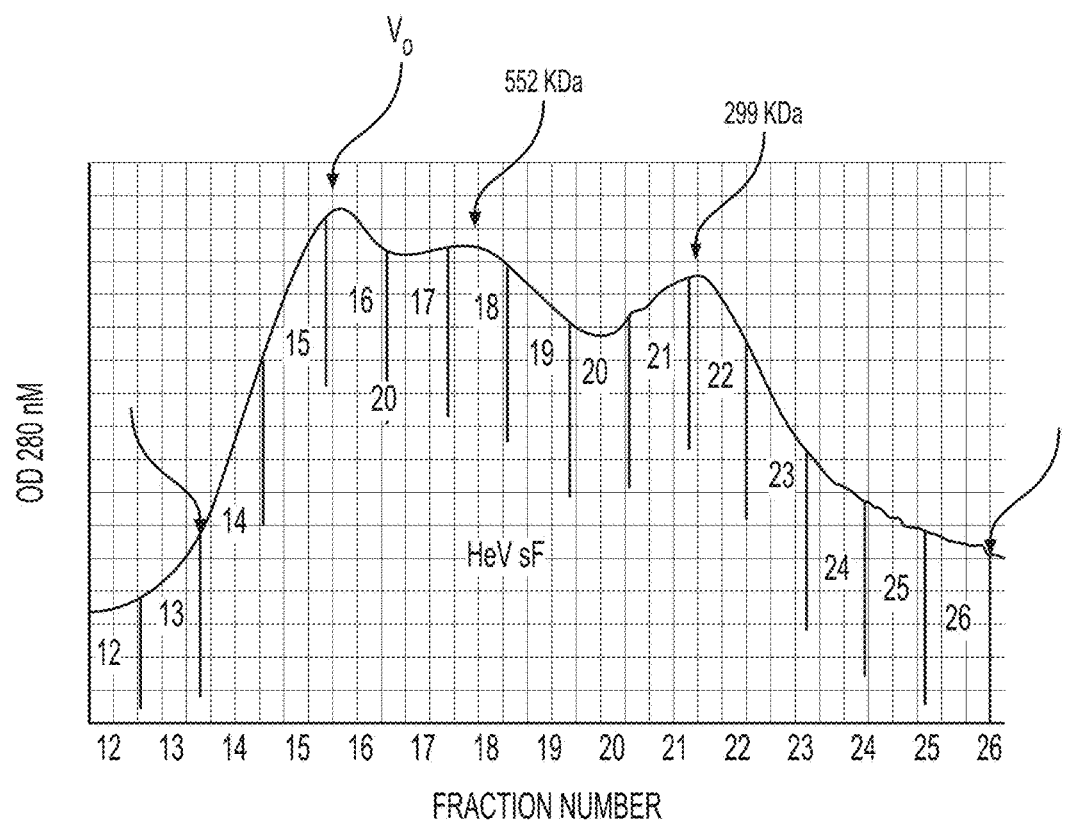
FIG. 1 shows size exclusion chromatography analysis of HeV soluble F (sF) glycoprotein. 300 μg of HeV sF glycoprotein was analyzed on a calibrated Superdex™ 200 10/300 gel filtration column. 400 μL fractions were collected. The elution volume of each peak was used to determine the approximate molecular mass as depicted from the calibrated curve. Vo indicates the void volume.

The Hendra virus (HeV) and Nipah virus (NiV) are closely related members of the *Henipavirus* genus of the Paramyxoviridae family. These viruses infect cells by a pH-independent membrane fusion event mediated by their attachment (G) and fusion (F) envelope glycoproteins (Envs). Generally, this invention provides soluble forms of HeV and NiV F glycoprotein, the nucleotide sequences encoding the proteins and to methods for using these proteins to diagnose, detect, prevent, and treat disease associated with infection by HeV and/or NiV. Specifically, this invention provides soluble forms of HeV and NiV F glycoprotein which retain characteristics of the native F glycoprotein.

The natural physiology of the F glycoprotein amino acid sequence prevents the protein from being soluble in aqueous solutions. The present invention provides soluble forms of the HeV and NiV F glycoproteins comprising all or part of the extracellular domain of F glycoprotein of a HeV or NiV. The soluble forms of F glycoprotein may be produced by deleting all or part of the transmembrane and cytoplasmic tail domains of the F glycoprotein. By way of example, a soluble F glycoprotein may comprise the complete extracellular region of an HeV or NiV F glycoprotein. Also, by way of example, a soluble F glycoprotein may comprise all or part of the extracellular region and part of the transmembrane domain of an HeV or NiV F glycoprotein. By way of further example, several versions of a soluble F (sF) glycoprotein were constructed, primarily through removing the cytoplasmic tail and/or transmembrane domain that anchor the protein. Without these regions, the resulting expressed F glycoprotein is soluble.

The sF glycoproteins of the invention are structurally similar to the native viral F glycoprotein. By way of example, the sF glycoproteins of the invention may be recognized by polyclonal antibodies directed to HeV and/or NiV. By way of example, the sF glycoproteins of the invention may assemble in the oligomeric form or forms (such as a trimer), comparable to native NiV and HeV F glycoprotein.

The sF glycoproteins of the present invention are suitable, for example, for vaccine development and for acting as an antigen to generate anti-viral antibodies when used as a vaccine or in the isolation of recombinant monoclonal antibodies. The sF glycoproteins are suitable to generate antibodies capable of recognizing native F glycoprotein. The sF glycoproteins of the present invention that assemble in oligomeric forms, such as trimers, can be of further use, such as, for example, for crystallization and structural determination to provide further information to aid structural-based antiviral research. The oligomeric forms of sF glycoprotein of the present invention may also generate further antibodies capable of recognizing native F glycoprotein and its native oligomeric forms. Examples of methodology that may be used include, but are not limited to, the assays described herein in the Examples.

As used herein, the singular form "a" or "an" "the" includes plural references unless indicated otherwise. For example, "a" F glycoprotein includes one or more F glycoproteins.

As used herein, "soluble F glycoprotein" or "soluble form of F glycoprotein" or "sF glycoprotein" refers to an amino acid sequence corresponding to a fragment or portion of native F glycoprotein that contains the extracellular domain or a portion thereof. The sF glycoprotein is structurally similar to the native viral F glycoprotein. By way of example, removal of a transmembrane domain increases solubility.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the team "antibody" means not only full-length immunoglobulin molecules but also antigen binding active fragments such as the well-known active fragments F(ab')2, Fab, Fv, and Fd.

As used herein, the terms "Hendra Virus Disease" and "Nipah Virus Disease" refer to diseases caused, directly or indirectly, by infection with Hendra or Nipah virus. The broad species tropisms and the ability to cause fatal disease in both animals and humans have distinguished Hendra virus (HeV) and Nipah virus (NiV) from all other known paramyxoviruses (Eaton (2001) Microbes. Infect. 3:277-278). These viruses can be amplified and cause disease in large animals and can be transmitted to humans where infection is manifested as a severe respiratory illness and/or febrile encephalitis.

As used herein with respect to proteins and polypeptides, the term "recombinant" may include proteins and/or polypeptides and/or peptides that are produced or derived by genetic engineering, for example by translation in a cell of non-native nucleic acid or that are assembled by artificial means or mechanisms.

As used herein with respect to polypeptides and proteins, the term "isolated" may include a polypeptide or nucleic acid that, by the hand of man, exists apart from its native environment and is therefore not a product of nature. For example, an isolated polypeptide may exist in a purified form or may exist in a non-native environment such as, for example, a recombinant host cell.

As used herein, the term "analog" may include any polypeptide having an amino acid sequence substantially identical to a polypeptide, or peptide, of the invention, in which one or more residues have been conservatively substituted with a functionally similar residue, and further which displays substantially identical functional aspects of the polypeptides as described herein. Examples of conservative substitutions include substitution of one non-polar (hydrophobic) residue for another (e.g. isoleucine, valine, leucine or methionine) for another, substitution of one polar (hydrophilic) residue for another (e.g. between arginine and lysine, between glutamine and asparagine, between glycine and serine), substitution of one basic residue for another (e.g. lysine, arginine or histidine), or substitution of one acidic residue for another (e.g. aspartic acid or glutamic acid).

As used herein, a "homolog" may include any polypeptide having a tertiary structure substantially identical to a polypeptide of the invention which also displays the functional properties of the polypeptides as described herein.

As used herein, "trimerization domain" refers to a structural motif that aids the polymerization of expressed proteins. Trimerization domains may aid soluble proteins to configure as though they were bound to the membrane. Trimerization domains, for example, may use coiled-coil motifs to polymerize. An example of a trimerization domain is seen in the basic leucine zipper. Basic leucine zippers typically correlate to a coiled coil of α-helices, whereby the positioning of leucine, or other hydrophobic amino acids, in the helices interact to form a hydrophobic core. An example of a basic leucine zipper is GCN4.

As used herein "treatment" may include any type of intervention used in an attempt to alter the natural course of the individual or cell. Treatment may include, but is not limited to, administration of e.g., a pharmaceutical composition, alone or in combination with other treatment modalities generally known in the art. The "treatment" may be performed prophylactically, or subsequent to the initiation of a pathologic event.

As used herein, "pharmaceutically acceptable carrier" may include any material which, when combined with an active ingredient, allows the ingredient to retain biological activity and is non-reactive with the subject's immune system. Examples may include, but are not limited to, standard pharmaceutical carriers such as a phosphate buffered saline (PBS) solution, water, emulsions, and various types of wetting agents.

As used herein, "fusion" may refer to nucleic acids and polypeptides that comprise sequences that are not found naturally associated with each other in the order or context in which they are placed according to the present invention. A fusion nucleic acid or polypeptide does not necessarily comprise the natural sequence of the nucleic acid or polypeptide in its entirety. Fusion proteins have the two or more segments joined together through normal peptide bonds. Fusion nucleic acids have the two or more segments joined together through normal phosphodiester bonds.

As used herein, "subject" may include the recipient of the treatment to be practiced according to the invention. The subject can be any animal, including a vertebrate. The subject will in most cases, preferably be a human, but may also be a domestic livestock, laboratory animal (including but not limited to, rodents such as a rat or mouse) or pet animal.

As used herein, "cleavage" may refer to the severing of an amino acid or nucleotide sequence. By way of example, cleavage may occur with the use of enzymes, such as trypsin and chymotrypsin. By way of further example, nucleotide sequences can be cleaved with the use of restriction endonucleases.

Nipah and Hendra viruses require the concerted action of the attachment and fusion glycoproteins to infect the host cell and insert the nucleocapsid. The present invention provides a soluble form of the F glycoprotein of both the Nipah and Hendra viruses. For example, the absence of the cytoplasmic and transmembrane regions of the carboxyl terminus of the F glycoprotein allow for solubilization of the protein. As a further example, use of the first 488 amino acids of NiV and HeV (a loss of 58 amino acids in both), produces a soluble version of the F glycoprotein that retains characteristics of the native protein. The present invention includes polypeptides and fragments and analogs and homologs thereof having substantially the same function as the polypeptides of this invention. This invention also encompasses proteins or peptides that are substantially homologous to the polypeptides.

Soluble Forms of the F Glycoprotein of NiV and HeV

The present invention provides soluble forms of NiV and HeV F glycoprotein from differing strains. The present invention provides soluble forms of the F glycoprotein comprising an amino acid sequence with significant homology to the amino acid sequences of the extracellular domain of native F glycoproteins of the Hendra and Nipah virus. In a further embodiment, the soluble forms of the F glycoprotein have at least 50% identity with native NiV or HeV F glycoprotein, preferably at least about 70% identity, more preferably at least about 80%, more preferably still at least about 90%, and most preferably at least about 98% sequence identity. In one embodiment, the polypeptide comprises SEQ ID NO: 2. In another embodiment, the polypeptide comprises SEQ ID NO: 4. The sF glycoproteins may further encompass amino acid insertions, substitutions and/or deletions that have minimal to no effect on the activity, function or shape of the polypeptide. Examples of such substitutions include the substitution of one non-polar residue for another, the substitution of one polar residue for another, the substitution of one basic residue for another, or the substitution of one acidic residue for another. The sF glycoprotein may further include insertions, substitutions and/or deletions of amino acids in a comparison to the amino acid sequence of the extracellular domain of native NiV or HeV F glycoprotein that yield minimal effect on the activity, function and/or structure of the polypeptide. Those skilled in the art will recognize non-natural amino acids may also be used. Non-natural amino acids include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sat), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); beta-2-thienylalanine (Thi); and methionine sulfoxide (MSO).

The sF glycoprotein of the present invention may be prepared by any known techniques. For example, the polypeptides may be expressed through genetic engineering. By way of example, the translation of recombinant DNA. The polypeptides may also be prepared synthetically. By way of example, the polypeptide may be synthesized using the solid-phase synthetic technique initially described by Merrifield (J. Am Chem. Soc. 85:2149-2154), which is incorporated herein by reference. Other polypeptide synthesis techniques may be found, for example, Kent et al. (1985) in Synthetic Peptides in Biology and Medicine, eds. Alitalo et al., Elsevier Science Publishers, 295-358.

The sF glycoprotein of the present invention may be isolated or obtained in substantially pure form. Substantially pure means that the proteins and/or polypeptides and/or peptides are essentially free of other substances with which they may be found in nature or in vivo systems to an extent practical and appropriate for their intended use. In particular, the sF glycoproteins are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

Fusion Polypeptides Comprising Soluble F Glycoprotein

The present invention further provides isolated fusion polypeptides comprising sF glycoprotein and additional polypeptides. The additional polypeptides may be fragments of a larger polypeptide. In one embodiment, there are one, two, three, four, or more additional polypeptides fused to the sF glycoprotein. In some embodiments, the additional polypeptides are fused toward the amino terminus of the sF glycoprotein. In other embodiments, the additional polypeptides are fused toward the carboxyl terminus of the sF glycoprotein. In further embodiments, the additional polypeptides flank the sF glycoprotein.

In some embodiments, the additional polypeptides aid the stabilization, structure and/or the purification of the sF glycoprotein. In some embodiments, the additional polypeptides assist the sF glycoprotein to form oligomers, such as a trimer. Oligomers may assist sF glycoproteins to configure in a manner more similar to native F glycoprotein. By way of example, a trimerization domain fused to sF glycoprotein may stabilize the polypeptide and may further increase polymerization of the polypeptide.

In some embodiments the additional polypeptides may comprise an epitope. In other embodiments, the additional polypeptides may comprise an affinity tag. By way of example, fusion of a polypeptide comprising an epitope and/or an affinity tag to sF glycoprotein may aid purification and/or identification of the polypeptide. By way of example, the polypeptide segment may be a His-tag, a myc-tag, an S-peptide tag, a MBP tag (maltose binding protein), a GST tag (glutathione S-transferase), a FLAG tag, a thioredoxin tag, a GFP tag (green fluorescent protein), a BCCP (biotin carboxyl carrier protein), a calmodulin tag, a Strep tag, an HSV-epitope tag, a V5-epitope tag, and a CBP tag. The use of such epitopes and affinity tags is known to those skilled in the art.

In further embodiments, the additional polypeptides may provide a fusion protein comprising sites for cleavage of the polypeptide. As an example, a polypeptide may be cleaved by hydrolysis of the peptide bond. In some embodiments, the cleavage is performed by an enzyme. In some embodiments cleavage occurs in the cell. In other embodiments, cleavage occurs through artificial manipulation and/or artificial introduction of a cleaving enzyme. By way of example, cleavage enzymes may include pepsin, trypsin, chymotrypsin, and/or Factor Xa. The additional polypeptides may provide for a membrane anchor domain. The membrane anchor domain may be a site for cleavage. For example, Phospholipase D will cleave the membrane anchor domain of SEQ ID NO: 8. Moreover, cleavage allows ease of isolating the sF glycoprotein from the polypeptides. Cleavage may also allow isolation of sF glycoprotein fused to polypeptides from other polypeptides. By way of example, a Factor Xa cleavage site may allow isolation of sF glycoprotein fused to a trimerization domain from an S-peptide tag. The present invention provides sF glycoprotein fused to a trimerization domain, a Factor Xa cleavage domain and an S-peptide tag. The trimerization domain allows for the association of sF glycoprotein as an oligomer. The S-peptide tag allows for purification through the use of anti-S-peptide antibodies. The Factor Xa cleavage domain allows for separation of the sF glycoprotein fused to the trimerization domain from the S-peptide tag.

Fusion polypeptides may further possess additional structural modifications not shared with the same organically synthesized peptide, such as adenylation, carboxylation, glycosylation, hydroxylation, methylation, phosphorylation or myristylation. These added structural modifications may be further be selected or preferred by the appropriate choice of recombinant expression system. On the other hand, fusion polypeptides may have their sequence extended by the principles and practice of organic synthesis.

Nucleic Acids Encoding Soluble Forms of F Glycoprotein

The present invention provides nucleic acid molecules encoding an amino acid sequence of a soluble form of the F glycoprotein of NiV or HeV and variants thereof. Nucleic acids may include single or double stranded forms of deoxyribonucleotides or ribonucleotides or polymers thereof.

The present invention also provides a vector comprising a nucleic acid encoding for the F glycoprotein of NiV or HeV. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Vectors may further contain a promoter sequence. A promoter may include an untranslated nucleic acid sequence usually located upstream of the coding region that contains the site for initiating transcription of the nucleic acid. The promoter region may also include other elements that act as regulators of gene expression. In further embodiments of the invention, the expression vector contains an additional region to aid in selection of cells that have the expression vector incorporated. The promoter sequence is often bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., □-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

An expression vector is one into which a desired nucleic acid sequence may be inserted by restriction and ligation such that it is operably joined to regulatory sequences and may be expressed as an RNA transcript. Expression refers to the transcription and/or translation of an endogenous gene, transgene or coding region in a cell.

A coding sequence and regulatory sequences are operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

Some aspects of the present invention include the transformation and/or transfection of nucleic acid encoding sF glycoprotein. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

Higher eukaryotic cell cultures may be used to express the proteins of the present invention, whether from vertebrate or invertebrate cells, including insects, and the procedures of propagation thereof are known (see, for example, Kruse et al. (1973) Tissue Culture, Academic Press).

Suitable host cells for expressing the polypeptides of the present invention in higher eukaryotes include: 293 (human embryonic kidney) (ATCC CRL-1573); 293F (Invitrogen, Carlsbad Calif.); 293T and derivative 293T/17 (293tsA1609neo and derivative ATCC CRL-11268) (human embryonic kidney transformed by SV40 T antigen); COS-7 (monkey kidney CVI line transformed by SV40)(ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

In other embodiments, the present invention provides nucleic acid molecules encoding a fusion protein comprising the sF glycoprotein and additional polypeptides. Vectors useful for constructing eukaryotic expression systems for the production of fusion polypeptides comprise nucleic acid encoding the fusion protein operatively linked to an appropriate transcriptional activation sequence, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

In some embodiments, the nucleic acid molecules encode a fusion protein comprising nucleic acids fused to the nucleic acid encoding the sF glycoprotein. The fused nucleic acid may encode polypeptides that may aid in purification and/or immunogenicity and/or stability without shifting the codon reading frame of the sF glycoprotein. In some embodiments, the fused nucleic acid will encode for a polypeptide to aid purification of the sF glycoprotein. In some embodiments the fused nucleic acid will encode for an epitope and/or an affinity tag. Examples of polypeptides that aid purification include, but are not limited to, a His-tag, a myc-tag, an S-peptide tag, a MBP tag, a GST tag, a FLAG tag, a thioredoxin tag, a GFP tag, a BCCP, a calmodulin tag, a Strep tag, an HSV-epitope tag, a V5-epitope tag, and a CBP tag.

In other embodiments, the fused nucleic acid will encode for a polypeptide that correlates to a site directed for, or prone to, cleavage. In preferred embodiments, the fused nucleic acid will encode for polypeptides that are sites of enzymatic cleavage. In further embodiments, the enzymatic cleavage will aid to isolate the sF glycoprotein, as well as other fused polypeptide segments, from yet other polypeptides. By way of example, an intermediary nucleic acid that encodes for an enzymatic cleavage site placed between nucleic acids that encode for sF glycoprotein and an S-peptide epitope will allow for later separation of the expressed sF glycoprotein and the S-peptide. In further preferred embodiments, the fused nucleic acid will encode in part for amino acids that are a site of cleavage by Factor Xa. In some embodiments, the fused nucleic acid will encode for amino acids that are membrane anchored and a site of cleavage. By way of example, SEQ ID NO: 8 will anchor the fusion polypeptide to the plasma membrane and is a site for Phospholipase D cleavage.

In other embodiments, the fused nucleic acid will encode in part for a polypeptide that aids the stability and function of the soluble F glycoprotein. In further embodiments, the fused nucleic acid will encode for polypeptides that aid in forming oligomers of soluble F glycoprotein. In preferred embodiments, the fused nucleic acid will encode for a trimerization domain. A basic leucine zipper motif is an example of a trimerization domain. By way of further example, the basic leucine zipper motif is a GCN4 polypeptide segment.

In other embodiments, the multiple nucleic acids will be fused to the nucleic acid encoding sF glycoprotein. The fused nucleic acids may encode for polypeptides that aid purification and/or enzymatic cleavage and/or stability. In further embodiments, the fused nucleic acids will not elongate the expressed polypeptide significantly. In further embodiments, the fused nucleic acids will encode for less than sixty extra amino acids to the sF glycoprotein. In some embodiments, the fused nucleic acids follow after the nucleic acid encoding the sF glycoprotein. In other embodiments, the fused nucleic acids precedes the nucleic acid encoding sF glycoprotein. In other embodiments, the fused nucleic acids flank the nucleic acid encoding sF glycoprotein. In some embodiments, a fused nucleic acid that encodes for an amino acid sequence prone to enzymatic cleavage and is placed between the nucleic acid that encodes for sF glycoprotein region and another fused nucleic acid that encodes for a polypeptide to aid purification. In preferred embodiments, the nucleic acid molecule will be arranged so that a cleavage domain will separate a polypeptide to aid purification from the sF glycoprotein fused to a trimerization domain.

Antibodies That Bind Soluble Forms of F Glycoprotein

Another aspect of the invention is directed to the generation of antibodies. Examples of antibodies encompassed by the present invention, include, but are not limited to, antibodies specific for HeV F glycoprotein, antibodies specific for NiV F glycoprotein, antibodies that cross react with HeV F glycoprotein and NiV F glycoprotein and neutralizing antibodies. The antibodies of the invention may be characterized using methods well known in the art.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. Preferred antibodies are derived from murine, rat, human, primate, or any other origin (including chimeric and humanized antibodies).

In one embodiment the antibodies are polyclonal or monoclonal antibodies. Methods of preparing monoclonal and polyclonal antibodies are well known in the art.

In other embodiments, the antibodies are humanized by methods known in the art. A humanized antibody is an immunoglobulin molecule that contains minimal sequence derived from non-human immunoglobulin. In yet other embodiments, fully human antibodies are obtained by using commercially available mice that have been engineered to express specific human immunoglobulin proteins. In other embodiments, the antibodies are chimeric. A chimeric antibody is an antibody that combines characteristics from two different antibodies. Methods of preparing chimeric antibodies are known in the art.

In other embodiments, the nucleotide sequence that encodes the antibody is obtained and then cloned into a vector for expression or propagation. In another embodiment, antibodies are made recombinantly and expressed using methods known in the art. By way of example, sF glycoprotein may be used as an antigen for the purposes of isolating recombinant antibodies by these techniques. Antibodies can be made recombinantly by using the gene sequence to express the antibody recombinantly in host cells. Methods for making derivatives of antibodies and recombinant antibodies are known in the art.

In other embodiments, the antibodies are bound to a carrier by conventional methods in the art, for use in, for example, isolating or purifying native Hendra or Nipah F glycoproteins or detecting native Hendra or Nipah F glycoproteins in a biological sample or specimen. In other embodiments, neutralizing antibodies are administered as passive immunotherapy to a subject infected with or suspected of being infected with Hendra or Nipah virus.

An antibody is a heterotetrameric glycoprotein composed of two identical light (L) chains and two identical heavy (H) chains (an IgM antibody consists of five of the basic heterotetramer unit along with an additional polypeptide called J chain, and therefore contain ten antigen binding sites, while secreted IgA antibodies can polymerize to form polyvalent assemblages comprising two to five of the basic four chain units along with J chain). The L chain from any vertebrate species can be assigned to one of two clearly distinct types, called kappa and lambda, based on the amino acid sequences of their constant domains and the methods of the current invention include the use of antibodies with either a kappa or lambda L chain. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha, delta, epsilon, gamma and mu, respectively. The gamma and alpha classes are further divided into subclasses on the basis of relatively minor differences in CH sequence and function, e.g., humans express the following subclasses:

IgG$_1$, IgG$_2$, IgG$_3$, IgG$_4$, IgA$_1$ and IgA$_2$. The methods of the present invention include the use of antibodies, including monoclonal antibodies, from any of the above classes and/or subclasses.

As used herein, the term "variable" refers to the fact that certain segments of the variable domains differ extensively in sequence among antibodies. The variable domain mediates antigen binding and defines specificity of a particular antibody for its particular antigen. However, the variability is not evenly distributed across the 110-amino acid span of the variable domains. Instead, the variable regions consist of relatively invariant stretches called framework regions (FR) of about fifteen to thirty amino acids separated by shorter regions of extreme variability called "hypervariable regions" that are each about nine to twelve amino acids long. The variable domains of native heavy and light chains each comprise four framework regions, largely adopting a beta-sheet configuration, connected by three hypervariable regions, which form loops connecting, and in some cases forming part of, the beta-sheet structure. The hypervariable regions in each chain are held together in close proximity by the framework region and, with the hypervariable regions from the other chain, contribute to the formation of the antigen-binding site of antibodies (see Kabat et al. (1991) Sequences of Proteins of Immunological Interest, Public Health Service, National Institutes of Health). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" which contributes to the specificity of the antibody.

The term "antibodies or fragments thereof" as used herein refers to antibodies or fragments thereof that specifically bind to a sF polypeptide or a fragment of a sF polypeptide and do not specifically bind to other non-sF polypeptides. Preferably, antibodies or fragments that immunospecifically bind to a sF polypeptide or fragment thereof do not non-specifically cross-react with other antigens (e.g., binding cannot be competed away with a non-sF protein, e.g., BSA in an appropriate immunoassay). Antibodies or fragments that immunospecifically bind to an sF polypeptide can be identified, for example, by immunoassays or other techniques known to those of skill in the art. Antibodies of the invention include, but are not limited to, synthetic antibodies, monoclonal antibodies, recombinantly produced antibodies, intrabodies, diabodies, multispecific antibodies (including bi-specific: antibodies), human antibodies, humanized antibodies, chimeric antibodies, single-chain Fvs (scFv) (including bi-specific scfvs), single chain antibodies, Fab' fragments, F(ab')2 fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, i.e., molecules that contain an antigen binding site that immunospecifically binds to an sF antigen (e.g., one or more complementarity determining regions (CDRs) of an anti-sF antibody).

The term "monoclonal antibody" as used herein refers to an antibody obtained from a population of substantially homogeneous antibodies, i.e., the individual antibodies comprising the population are identical except for possible naturally occurring mutations that may be present in minor amounts and includes antibody fragments as defined herein. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al. (1975) Nature 256, 495 or may be made using recombinant DNA methods in bacterial, eukaryotic animal or plant cells (see U.S. Pat. No. 4,816, 567). The "monoclonal antibodies" may also be isolated from phage antibody libraries using the techniques described in Clackson et al. (1991) Nature 352:624-628 and Marks et al. (1991) J. Mol. Biol. 222, 581-597, for example.

As used herein, an "intact" antibody is one which comprises an antigen-binding site as well as a $C_L$ and at least heavy chain constant domains, $C_{H1}$ and $C_{H2}$, and $C_{H3}$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding CDR or variable region of the intact antibody. Examples of antibody fragments include Fab, Fv, Fab' and F(ab')$_2$ fragments; diabodies; linear antibodies (see U.S. Pat. No. 5,641,870 and Zapata et al. (1995) Protein Eng. 8, 1057-1062); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_{H1}$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_{H1}$ domain including one or more cysteines from the antibody hinge region. Fab'-S$_H$ is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

As used herein, "Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

As used herein, "Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding (see Rosenburg et a (1994) The Pharmacology of Monoclonal Antibodies, Springer-Verlag, pp. 269-315).

As used herein, the term "diabodies" refers to small antibody fragments prepared by constructing sFv fragments (see preceding paragraph) with short linkers (about 5 to about 10 residues between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, WO 93/11161 and Hollinger et al. (1993) Proc. Natl. Acad. Sci. USA 90, 6444-6448.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous components. In preferred embodiments, the antibody will be purified to greater than 95% by weight of antibody, and most preferably more than 99% by weight. Isolated antibody includes the antibody in situ within recombinant cells since at least one component of the antibody's natural environment will not be present. Ordinarily, however, isolated antibody will be prepared by at least one purification step.

In one embodiment of the invention, the conjugated antibody binds to an epitope on the cytoplasmic domain of a protein specific to cancer cells (i.e., a cancer cell marker). In another embodiment, the conjugated antibody includes, but is not limited to, an antibody which binds to an epitope on the cytoplasmic domain of sF.

Pharmaceutical Compositions Comprising sF Glycoprotein

Another aspect of the invention is directed toward the use of the soluble F glycoprotein as part of a pharmaceutical composition. The antibodies and nucleic acids of the present invention may also be used as part of a pharmaceutical composition. The compositions used in the methods of the invention generally comprise, by way of example and not limitation, and effective amount of a nucleic acid or polypeptide (e.g., an amount sufficient to induce an immune response) of the invention or antibody of the invention (e.g., an amount of a neutralizing antibody sufficient to mitigate infection, alleviate a symptom of infection and/or prevent infection). The nucleic acids, polypeptides, and antibodies of the invention can further comprise pharmaceutically acceptable carriers, excipients, or stabilizers known in the art (see generally Remington, (2005) The Science and Practice of Pharmacy, Lippincott, Williams and Wilkins).

The nucleic acids, polypeptides, and antibodies of the present invention may be in the form of lyophilized formulations or aqueous solutions. Acceptable carriers, excipients, or stabilizers may be nontoxic to recipients at the dosages and concentrations that are administered. Carriers, excipients or stabilizers may further comprise buffers. Examples of buffers include, but are not limited to, carbohydrates (such as monosaccharide and disaccharide), sugars (such as sucrose, mannitol, and sorbitol), phosphate, citrate, antioxidants (such as ascorbic acid and methionine), preservatives (such as phenol, butanol, benzanol; alkyl parabens, catechol, octadecyldimethylbenzyl ammonium chloride, hexamethoniuni chloride, resorcinol, cyclohexanol, 3-pentanol, benzalkonium chloride, benzethonium chloride, and m-cresol), low molecular weight polypeptides, proteins (such as serum albumin or immunoglobulins), hydrophilic polymers amino acids, chelating agents (such as EDTA), salt-forming counter-ions, metal complexes (such as Zn-protein complexes), and non-ionic surfactants (such as TWEEN™ and polyethylene glycol).

The pharmaceutical composition of the present invention can further comprise additional agents that serve to enhance and/or complement the desired effect. By way of example, to enhance the immunogenicity of a soluble F glycoprotein of the invention being administered as a subunit vaccine, the pharmaceutical composition may further comprise an adjuvant.

Vaccines for Henipaviruses

Another aspect of the invention is directed toward the use of the sF glycoprotein as vaccinating agent. The formulation of a vaccine or immunogenic compositions of the invention will employ an effective amount of the polypeptide antigen. That is, there will be included an amount of antigen which will cause the subject to produce a specific and sufficient immunological response so as to impart protection to the subject from subsequent exposure to Hendra or Nipah virus. In one embodiment, HeV or NiV sF glycoprotein, or a combination thereof, is administered by itself or in combination with an adjuvant.

Adjuvants include aluminum salts (alum), Complete Freund's Adjuvant (CFA), Incomplete Freund's Adjuvant (IFA), Muramyl dipeptide (MDP), synthetic analogues of MDP, N-acetylmuramyl-L-alanyl-D-isoglutamyl-L-alanine-2-[1,2-dipalmitoyl-s-glycero-3-(hydroxyphosphoryloxy)] ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter (see, for example, EP 0399843).

In some embodiments, the adjuvant comprises a Toll like receptor (TLR) 4 ligand, in combination with a saponin. The Toll like receptor (TLR) 4 ligand may be for example, an agonist such as a lipid A derivative particularly monophosphoryl lipid A or more particularly 3 Deacylated monophoshoryl lipid A (3 D-MPL). 3 D-MPL is sold under the trademark MPL® by Corixa Corporation and primarily promotes CD4+ T cell responses with an IFN-g (Th1) phenotype. It can be produced according to the methods disclosed in GB 2220211A. Chemically, it is a mixture of 3-deacylated monophosphoryl lipid A with 3, 4, 5 or 6 acylated chains. In one embodiment in the compositions of the present invention small particle 3 D-MPL is used. Small particle 3 D-MPL has a particle size such that it may be sterile-filtered through a 0.22 µm filter. Such preparations are described in PCT Patent Application WO 9421292.

The adjuvant may also comprise one or more synthetic derivatives of lipid A which are known to be TLR 4 agonists including, but not limited to: OM174 (2-deoxy-6-o-[2-deoxy-2-[(R)-3-dodecanoyloxytetra-decanoylamino]-4-o- phosphono-β-D-glucopyranosyl]-2-[(R)-3-hydroxytetradecanoylamino]-α-D-glucopyranosyldihydrogenphosphate), as described in PCT Patent Application WO 95/14026; OM 294 DP (3S, 9 R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate), as described in WO 9964301 and WO 00/0462; and, OM 197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other TLR4 ligands which may be used include, but are not limited to, alkyl Glucosaminide phosphates (AGPs) such as those disclosed in WO 98/50399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both can be used as one or more adjuvants in the compositions of the invention.

A preferred saponin for use in the present invention is Quil A and its derivatives. Quil A is a saponin preparation isolated from the South American tree Quilaja Saponaria Molina and was first described as having adjuvant activity by Dalsgaard et al. (1974) *Saponin adjuvants*, Archiv. für die gesamte Virusforschung, Vol. 44, Springer Verlag, pp. 243-254. Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of *Quillaja saponaria* Molina which induces CD8+ cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO 96/33739). The saponins forming part of the present invention may be separate in the form of micelles, mixed micelles (preferentially, but not exclusively with bile salts) or may be in the form of ISCOM matrices (EP 0109942 B1), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may be associated with a metallic salt, such as aluminium hydroxide or aluminium phosphate (WO 98/15287). In some embodiments, the saponin is presented in the form in of a liposome, ISCOM or an oil in water emulsion.

In some embodiments, adjuvants are combinations of 3D-MPL and QS21 (EP 0671948 B1) and oil in water emulsions comprising 3D-MPL and QS21 (WO 95/17210, WO 98/56414).

Other aspects contemplate use of sF glycoprotein as a subunit vaccine. A subunit vaccine refers to the use of a fragment of a virus as an inoculating agent. Those skilled in the art will know subunit vaccines offer a means to generate antibodies to a particular part or region of a virus. By way of example, a recombinant form of a surface receptor of a virus may serve as a subunit vaccine. A subunit vaccine comprising HeV or NiV soluble F glycoprotein, or combinations thereof, can be administered orally, intravenously, subcutaneously, intra-arterially, intramuscularly, intracardially, intraspinally, intrathoracically, intraperitoneally, intraventricularly, sublingually, and/or transdermally. Dosage schedule of administration and efficacy of subunit vaccines can be determined by methods known in the art.

Method of Using Soluble Forms of F Glycoprotein

One aspect of the present invention is directed in part to the treatment, the prevention, and the detection of NiV and/or HeV. In some embodiments, an animal receives treatment and/or prevention and/or detection of NiV and/or HeV. In preferred embodiments, the animal is a human. For example, the polypeptides of the present invention may be used to raise antibodies to NiV and/or HeV in vivo. By way of further example, the polypeptides of the present invention may be used to determine if a subject produces antibodies to NiV and/or HeV. In some embodiments, the polypeptide is used to isolate antibodies. By way of example, polypeptides may be bound to an affinity matrix.

By way of further example, the nucleic acid of the present invention can be used to transform and/transfect cells to recombinantly produce the polypeptides and/or antibodies of the present invention. The nucleic acids may further be utilized to treat an infected subject. By way of example, the nucleic acids can be used in inhibiting gene expression. The nucleic acids of the present invention may also be used, for example, to determine if a subject is infected with NiV and/or HeV. By way of example, this can be achieved using methods of radiolabeled hybridization.

By way of further example, the antibodies of the present invention can be used to recognize an infection by NiV and/or HeV. By way of example, the antibodies can recognize native F glycoprotein as an antigen. The antibodies of the present invention can also be used to fight an infection by NiV and/or HeV. By way of example, humanized antibodies or antibody fragments or monoclonal antibodies can employ a subject's own immune response to an NiV and/or HeV infection. By way of further example, the antibodies of the present invention may be coupled to a cytokine or a toxin or an enzyme or a marker to assist in treating and detecting an infection.

Further aspects of the present invention relate to diagnostic assays. The present invention is of use with many assays known in the art. Those skilled in the art will recognize the wide array of research based uses for the polypeptides, nucleic acids and antibodies of the present invention. The polypeptides, antibodies and nucleic acids of the present invention may, for example, be labeled, such as with a radioactive, chemiluminescent, fluorescent and/or dye molecules. The antibodies, nucleic acids and polypeptides of the present invention lend themselves to use in assays for example DNA assays (such as Southern blotting), RNA assays (such as northern blotting), protein assays (such as western blotting), chromatographic assays (such as gas, liquid, HPLC, size-exclusion), immunoassays (such as ELISA) and structural assays (such as crystallography and NMR spectroscopy). The antibodies, polypeptides and nucleic acids of the present invention may further be used as probes. Assays which amplify the signals from a probe are also known to those skilled in the art.

Diagnostic Kits Comprising Soluble Forms of F Glycoprotein

Another aspect of the invention is directed toward use of the sF glycoprotein as part of a kit used to detect the presence of Hendra or Nipah virus. Kits of the invention include one or more containers comprising by way of example, and not limitation, nucleic acids encoding a HeV or NiV sF glycoprotein or combinations thereof, a HeV or NiV sF glycoprotein or combinations thereof and/or antibodies of the invention and instructions for use in accordance with any of the methods of the invention described herein. The sF glycoproteins and/or antibodies of the invention may be used in a variety of immunoassays for Hendra and Nipah virus. In one embodiment, recombinant sF glycoprotein serves to function as an antigen for the purposes of detecting antibody in biological samples. The containers may be unit doses, bulk packages (e.g., multi-dose packages) or sub-unit doses. The kits of this invention are in suitable packaging. Also contemplated are packages for use in combination with a specific device, such as an inhaler, nasal administration device or an infusion device. A kit may have a sterile access port. The container may also have a sterile access port. Kits may optionally provide additional components such as buffers and interpretive information.

Without further description, it is believed that a person of ordinary skill in the art can, using the preceding description and the following illustrative examples, make and utilize the invention and practice the claimed methods. For example, a skilled artisan would readily be able to determine the administration of the food product of the present invention. The following working examples therefore, specifically point out the illustrative embodiments of the invention, and are not to be construed as limiting in any way the remainder of the disclosure.

EXAMPLES

All of the sF constructs described in the examples below were engineered using a modified version of the commercially available expression vector pcDNA 3.1 Hygo (+) (Invitrogen Corp.). The Hygromycin selection marker allows for selection of successfully transfected cells in the presence of the Geneticin (G418) antibiotic. The pcDNA 3.1 Hygro (+) was modified by incorporating the enhanced cytomegalovirus (CMV) promoter region from phCMV 1 (Gelantis). This enhanced CMV promoter allows for high expression of the sequences inserted into the backbone of the pcDNA 3.1 Hygro(+) vector. The addition of nucleic acid sequence to encode for an S-peptide sequence (SEQ ID NO: 5) facilitated purification of the released sF glycoprotein. Further nucleic acids sequences were introduced in some versions that would result in encoding additional peptide regions, such as a GPI-Phospholipase D cleavage site (SEQ ID NO: 7) a trimeric GCN4 motif (SEQ ID NO: 9) and a Factor Xa cleavage site (SEQ ID NO: 11). Expression plasmid constructs were generated with these nucleic acid sequences and used to generate stable cell lines that express the various versions of the proteins. The S-peptide 13 amino acid sequence (Novagen) was added to the C-terminus in all constructs. The S-peptide expression facilitates purification by S-protein agarose (Novagen), as well as immuno-detection by anti S-peptide antibodies.

Example 1: Production HeV sF Glycoprotein Trimer and Detection By Size Exclusion Chromatography Materials and Methods.
293T cells were transfected with the modified pcDNA 3.1 Hygro (+) vector containing an insert to encode for the first 488 amino acids of the F glycoprotein from HeV, followed by an S-peptide sequence. Selection for transfection was performed using Geneticin (G418), and surviving cells were maintained in the presence of G418 using standard tissue culture protocols. Cells and media were harvested by standard protocols. The resulting solutions were resolved by size exclusion chromatography, using a Superdex™ 200 10/300 gel filtration column, with 400 µL fractions collected.
Results.
The elution profile by gel filtration shows a putative trimer peak that elutes at ~299 kDA, a higher molecular weight species with a peak of ~552 kDa, and larger aggregates that elute near the void volume (Vo) (FIG. 1).

Example 2: Production of NiV sF Glycoprotein By Phospholipase D Cleavage

Figures 2A, 2B:
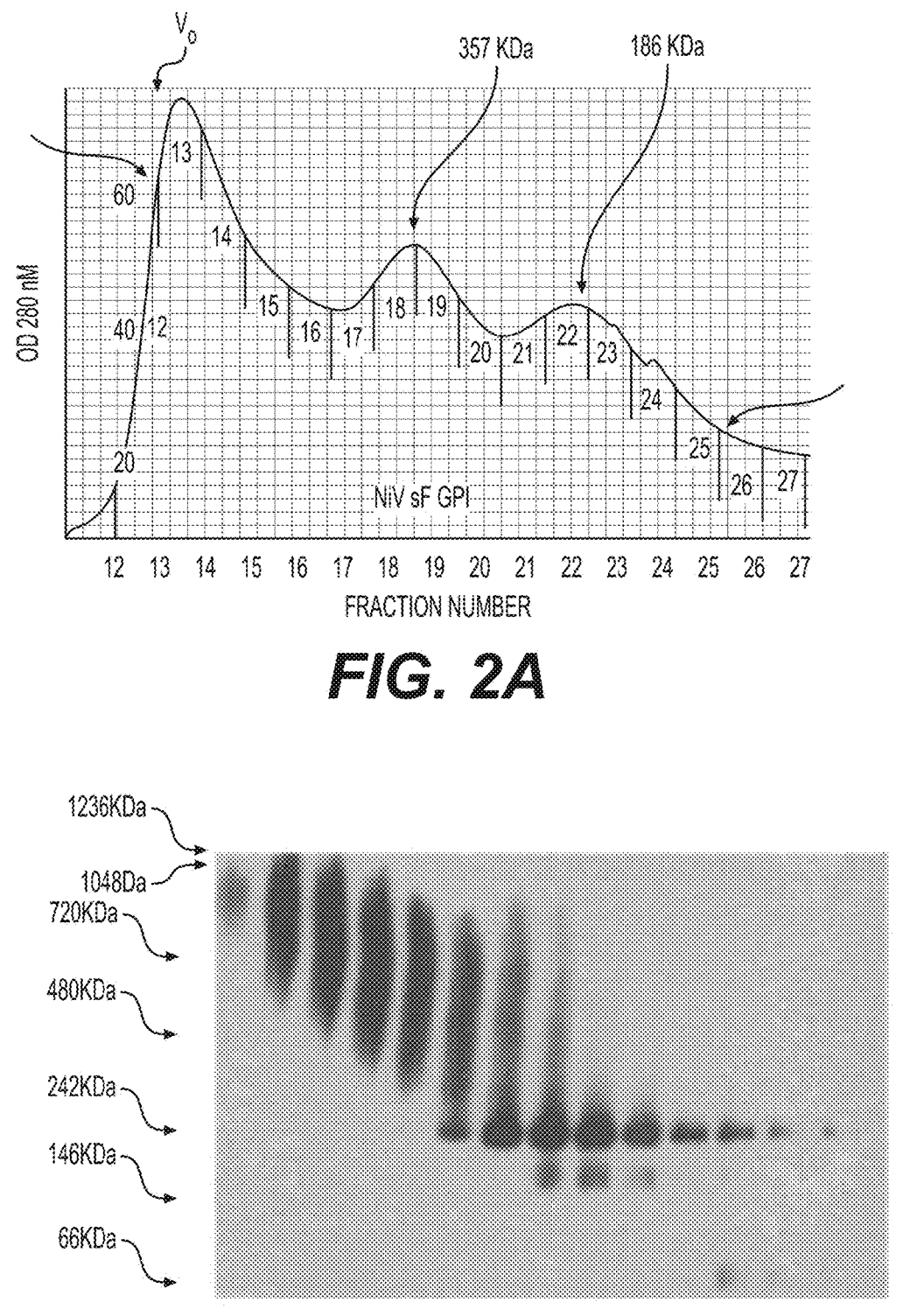

Materials and Methods.
As secretion of native NiV sF was poor, a modified version of NiV sF was engineered, whereby a glycoylphosphatidylinositol (GPI) anchor signal sequence was appended to the NiV sF nucleotide sequence. HeLa-PLD cells are a modified version of HeLa cells that stably express Phospholipase D (PLD) (Mann (2004) Biochem. J. 378: 641-648). PLD then specifically cleaves the phospho-glycerol bond in GPI-anchored proteins. This results in the release of GPI-linked proteins from the anchoring membrane. This mechanism then causes secretion of the previously GPI-anchored NiV sF GPI from the HeLa PLD cells.
HeLa-PLD cells were transfected with the modified pcDNA 3.1 Hygro (+) vector containing an insert to encode for the first 488 amino acids of the F glycoprotein from NiV, followed by an S-peptide sequence and then a GPI sequence to allow for PLD cleavage. Selection for transfection was performed using Geneticin (G418), and surviving cells were maintained in the presence of G418 using standard tissue culture protocols. Cells and media were harvested by standard protocols. The resulting solutions were resolved by size exclusion chromatography, using a Superdex™ 200 10/300 gel filtration column, with 400 µL fractions collected. 5 µL samples of each fraction were denatured and resolved by BN-PAGE. The resulting gel was transferred to a membrane, and following standard blocking and washing protocols, was probed with antibodies to the S-peptide sequence that are conjugated to HRP to allow for standard chemiluminescent detection.
Results.
The elution profile from the gel filtration of the NiV sF GPI construct shows a putative trimer peak that elutes at ~186 kDa, a higher molecular weight species with a peak of ~357 kDa, and larger aggregates that elute near the void volume (Vo) (FIG. 2A).

Example 3: Stabilization of HeV and NiV sF Glycoprotein Trimers By GCN4 Motif Materials and Methods.
293T cells were transfected with the modified pcDNA 3.1 Hygro (+) vector containing an insert to encode for the first 488 amino acids of the F glycoprotein from NiV or HeV, followed by a GCN sequence, then a Factor Xa cleavage sequence and then an S-peptide sequence. Selection for transfection was performed using Geneticin (G418), and surviving cells were maintained in the presence of G418 using standard tissue culture protocols. Cells and media were harvested by standard protocols. The resulting solutions were resolved by size exclusion chromatography, using a Superdex™ 200 10/300 gel filtration column, with 400 µL fractions collected. 5 µL samples of each fraction were denatured and resolved by BN-PAGE. The resulting gel was transferred to nitrocellulose paper, and following standard blocking and washing protocols, was probed with antibodies to the S-peptide sequence that are conjugated to HRP to allow for standard chemiluminescent detection.
Results.
Expression and secretion of HeV and NW sF glycoproteins containing a GCN4 motif was improved by at least 10-fold than their respective wild-type sF cells. This indicates the GCN4 motif affects codon optimization and stabilization of the sF.

Figure 3A:
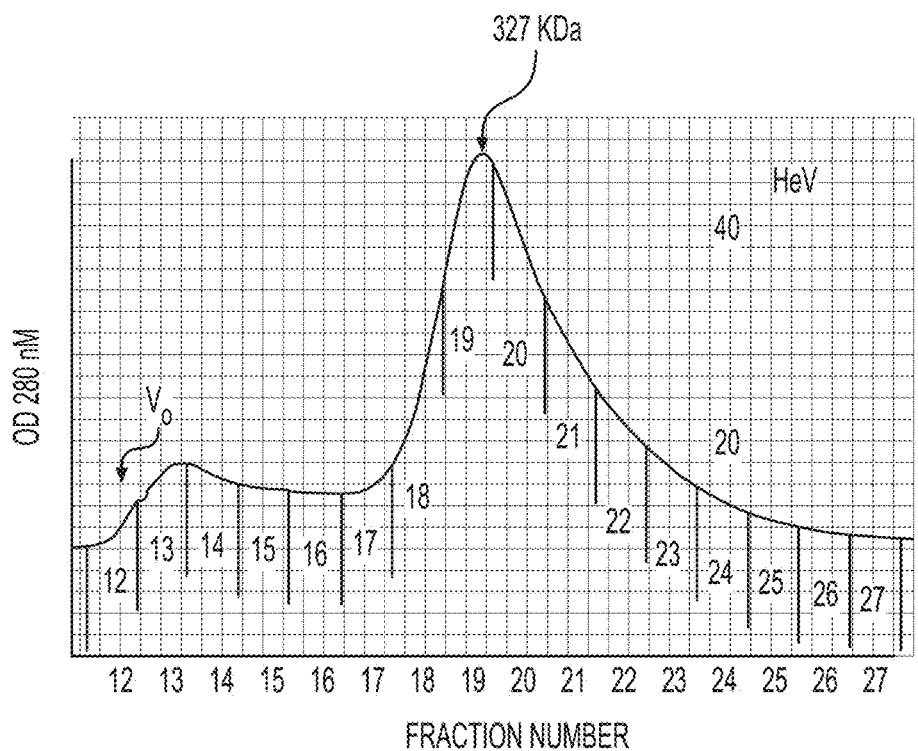
FIG. 3A shows 4 mg of HeV sF glycoprotein-GCN analyzed on a calibrated Superdex™200 10/300 gel filtration column. 400 μL fractions were collected. The elution volume of each peak was used to determine the approximate molecular mass as depicted from the calibrated curve. Vo indicates the void volume.
Figure 3B:
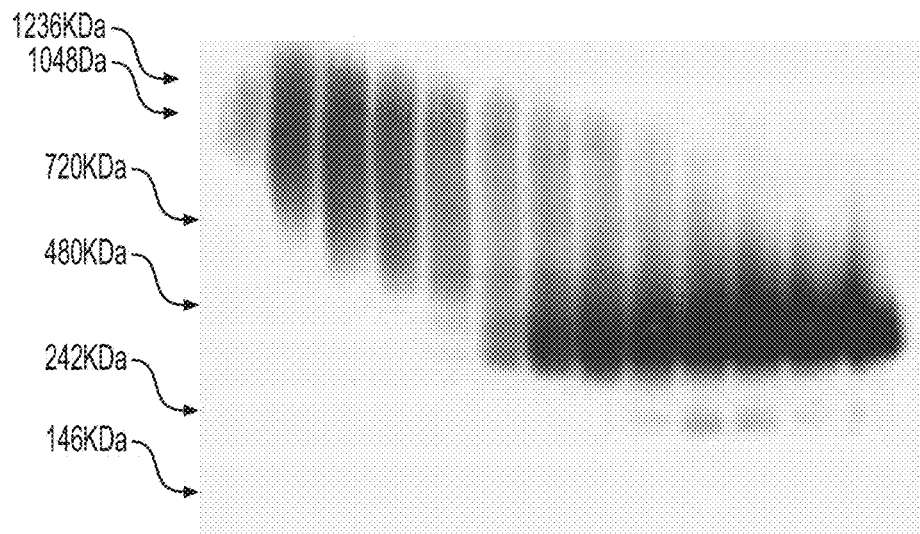
FIG. 3B shows 2 μL of each fraction analyzed by BN-PAGE followed by western blotting. Detection was done using HRP conjugated anti S-peptide antibody.
Figure 4A:
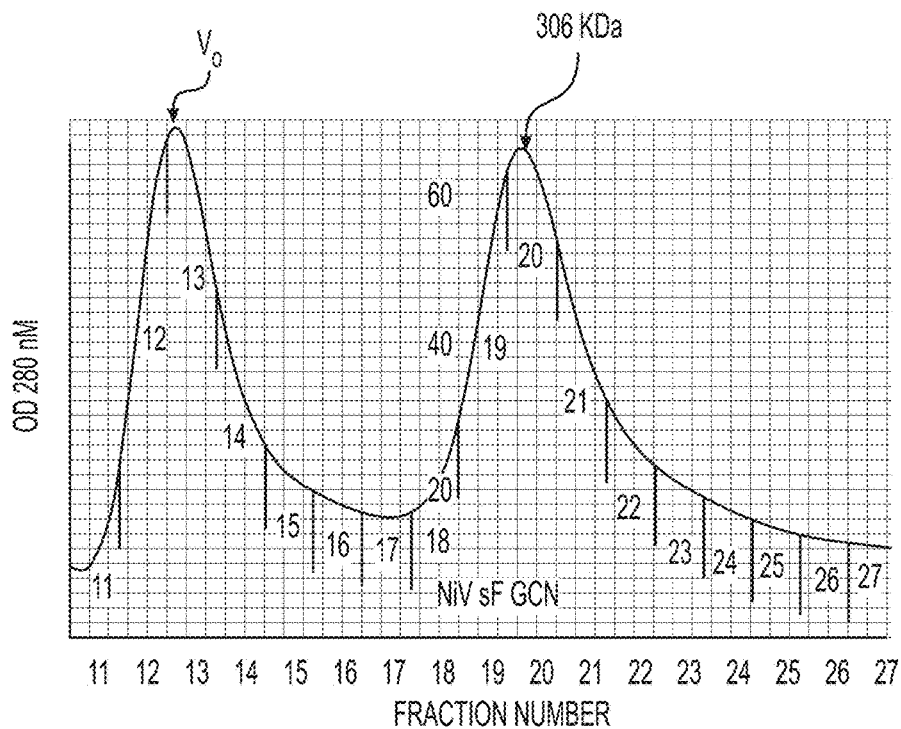
FIG. 4A shows 3 mg of NiV sF glycoprotein-GCN analyzed on a calibrated Superdex™ 200 10/300 gel filtration column. 400 μL fractions were collected. The elution volume of each peak was used to determine the approximate molecular mass as depicted from the calibrated curve. Vo indicates the void volume.
Figure 4B:
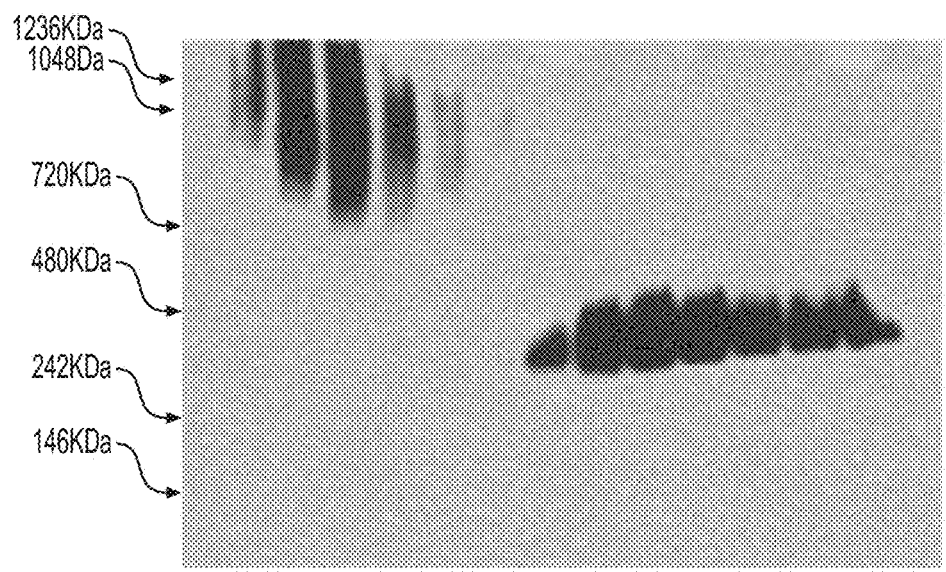
FIG. 4B shows 2 μL of each fraction analyzed by BN-PAGE followed by western blotting. Detection was done using HRP conjugated anti S-peptide antibody.

Differences can also be seen in the elution profiles between wild type sF and sF-GCN. The higher oligomeric species observed in the wild-type sF profiles was absent in the sF-GCN. A high aggregate species and a single putative trimer peak that elute at approximately 327 and 306 kDa was observed for HeV and NiV sF-GCN, respectively (FIG. 3A and FIG. 4A). The aggregate species for HeV sF-GCN was much lesser as compared to all the other sF. This suggests the trimer stabilization by the GCN motif eliminates higher oligomeric forms that present in the non-GCN sF. Native gel analysis using the Blue Native (BN) PAGE system (Invitrogen) of all the sF and the fractions from all gel filtrations show corresponding sizes of the trimer species (FIGS. 2-4B and FIG. 5), except for NiV sF GPI, which has a higher apparent molecular mass in Native gel as compared to the gel filtration analysis (FIG. 4).

Example 4: HeV and NiV sF Glycoproteins are Immunogenic in Mice and can Elicit Cross-Reactive and Neutralizing Polyclonal Antibody Responses Materials and Methods.

HeV sF S tagged and sF-GCN, and NiV sF-GPI S tagged and sF-GCN were used to immunize Balb/C mice. Each mouse was bled prior to immunization to obtain serum as negative control. Each mouse was primed and boosted 3 times with different sF preparations as indicated in Table 1. Each immunization was performed with 10 µg of protein using TiterMax® Gold Adjuvant (Sigma) with 28 days intervals. The mice were bled 10 days post immunization and serum samples were harvested. The serum collected from the second and third boost were pooled and examined by ELISA. The sF immunized mouse sera were also tested for its ability to immunoprecipitate full length untagged HeV and NiV F. The sF immunized mouse sera were also tested for an ability to neutralize NiV pseudotyped retroviral luciferase reporter virions.

Figure 5B:
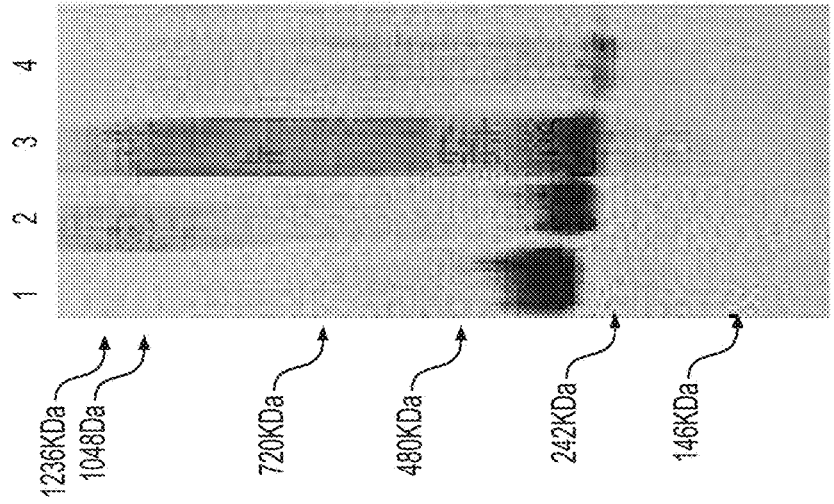
FIGS. 5A-5B show BN PAGE analysis of sF glycoprotein. In lane 1, HeV sF glycoprotein-GCN was loaded. In lane 2, NiV sF glycoprotein-GCN was loaded. In lane 3, HeV sF glycoprotein was loaded. In lane 4, NiV sF glycoprotein-GPI was loaded.
Figure 5A:
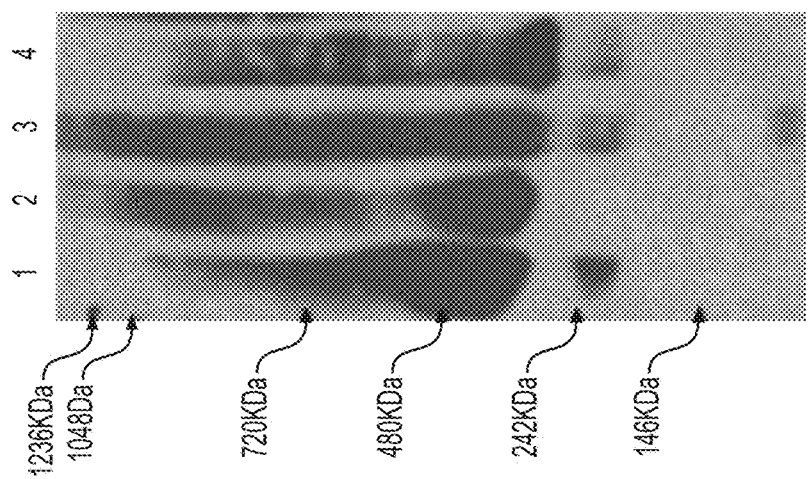
Figure 6A:
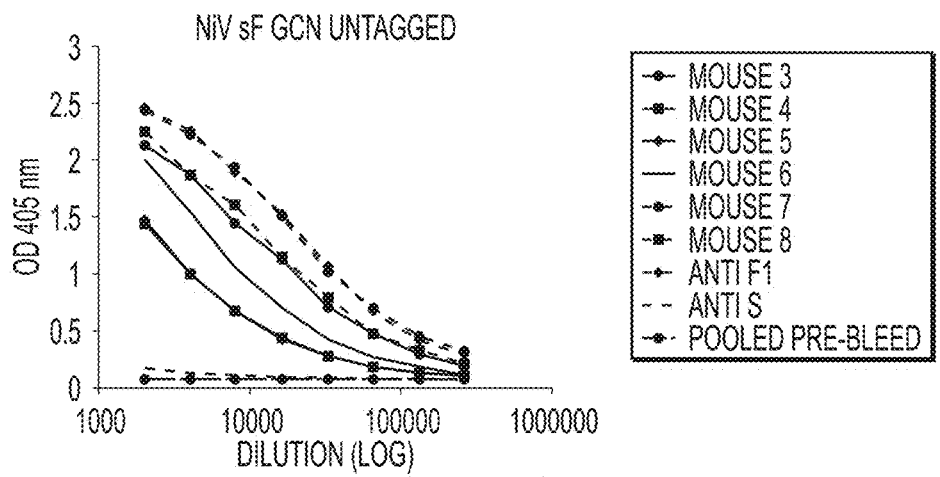
FIGS. 6A-6C show ELISA titration of serum from mice immunized with different sF protein as indicated in Table 1. Plates were coated with 50 ng of HeV (FIG. 6A) or NiV (FIG. 6B) sF GCN per well followed by blocking in 5% BSA, PBS, 0.05% Tween 20. Two-fold serial dilution starting from 1/2000 of each mouse serum, mAb D54 against HIV-1 envelope-GCN, anti S peptide antibody, and Rabbit anti HeV F1 polyclonal antibody was carried out. HRP conjugated anti mouse IgG was used as secondary antibody. Each serum titration was done in duplicates and the average OD values were plotted against the serum dilution in log values. HIV-1 envelope-GCN (FIG. 6C) was used to monitor the titer of antibody generated against the GCN tail.
Figure 6B:
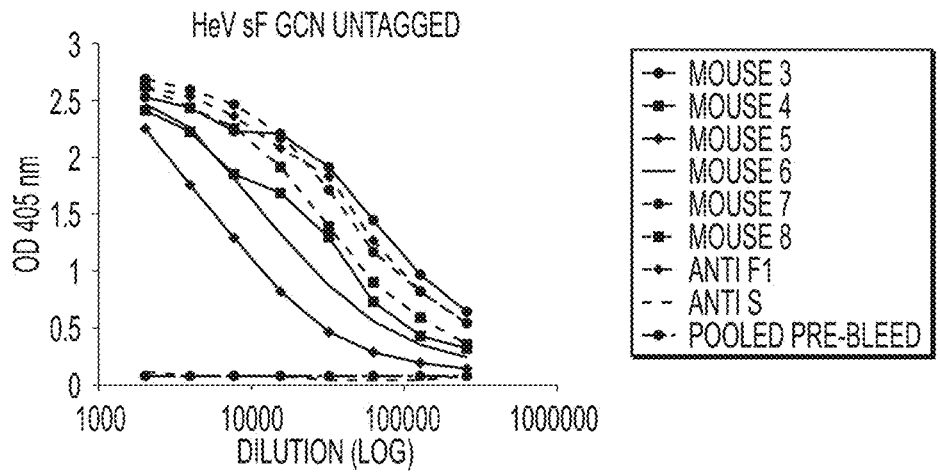
Figure 6C:
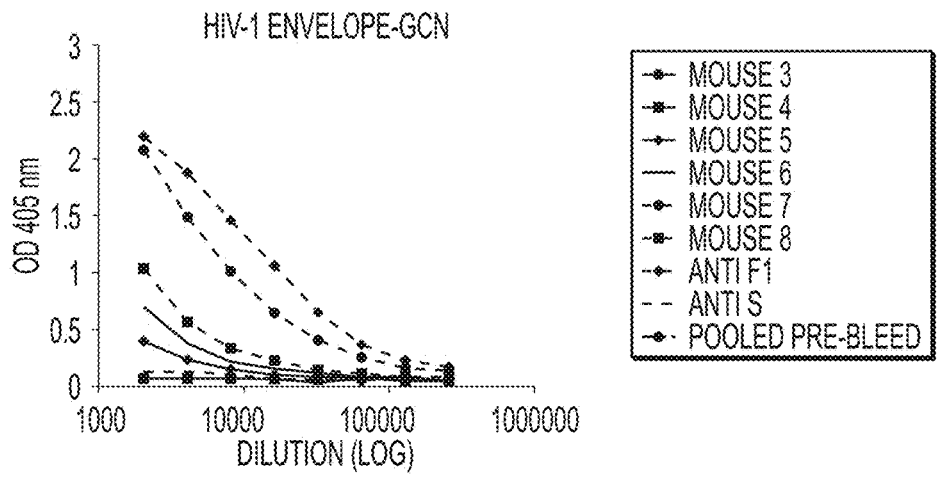
Figure 7:
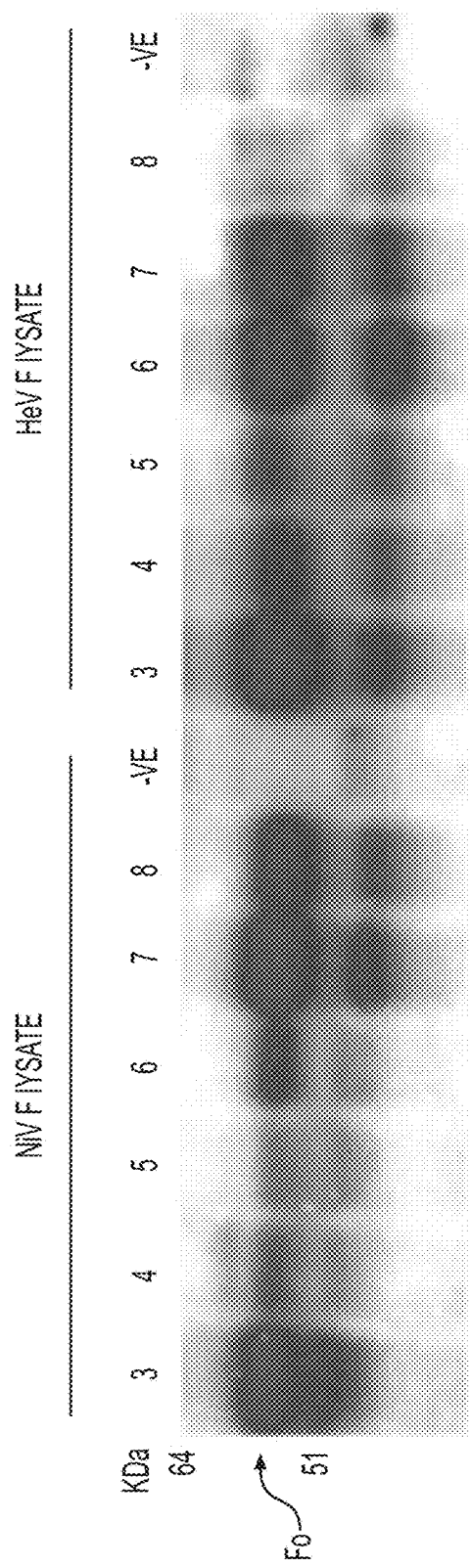
FIG. 7 shows immunoprecipitation of full length HeV or NiV F by different mouse serum. HeLa USU cells were infected with recombinant vaccinia virus expressing full length HeV or NiV F with MOI of 10 for 24 hours. Cells were lysed and cleared by centrifugation. The lysates were then divided equally into 7 portions. Each cell lysate fraction was then added with 1 µl of serum from different mouse immunized with different sF as indicated in Table 1. The mixture was rotated at 4° C. overnight followed by protein-G bead precipitation at room temperature for 1 hr. The bound complex was then washed 3 times and subsequently boiled in 50 µl SDS-PAGE sample loading buffer in reducing condition. 25 µl of the boiled samples were then analyzed on SDS-PAGE followed by western blotting. The precipitated F glycoprotein was detected using rabbit anti HeV F1 polyclonal antibody. (-ve indicates pooled pre-immunization serum).
Figure 8:
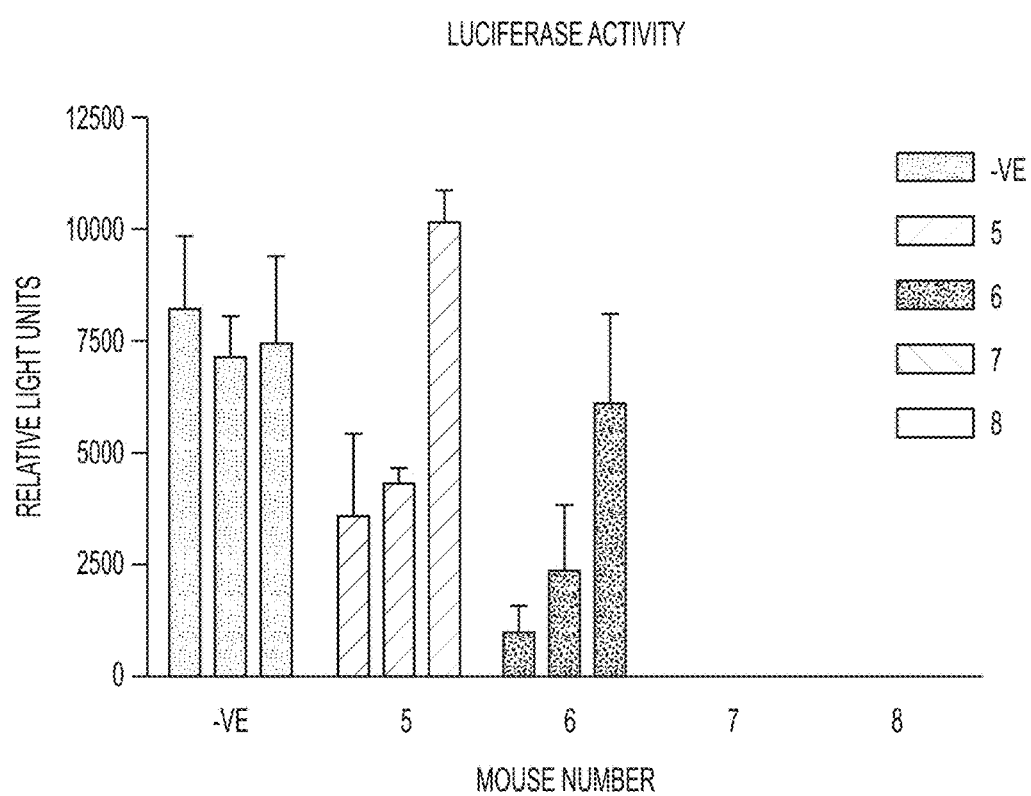
FIG. 8 shows serum neutralization of NiV F and G pseudotyped luciferase reporter virus. NiV F and G pseudovirus particles harboring the NL43 luciferase reporter gene was pre-incubated with the mouse serum in 1/200, 1/400, and 1/800 (left to right) dilution at room temperature for ½ hr. 293T cells were then infected with the mixture for 48 hrs. The cells were then lysed and the luciferase activity was measured. Each infection was done in triplicates. (-ve indicates pooled pre-immunization serum).

HeV and NiV F-specific cross-reactive antibody was observed in all mice as indicated in the ELISA assay (FIGS. 6A and 6B) and as demonstrated by the immunoprecipitation assay conducted with full-length HeV and NiV F (FIG. 7). A lower titer antibody response against the GCN tail was evident when a non-related (HIV-) envelope glycoprotein-(GCN) protein was used to coat the plate (FIG. 5C). Mice that were immunized with the non GCN sF showed no reactivity against HIV-1 envelope-GCN. Neutralizing and cross-reactive neutralizing antibodies were also generated as indicated by the neutralization of luciferase gene encoding retrovirus pseudotyped with NiV F and G entry assay. The assay was carried out using serum dilutions (Table 2) from mice immunized with the sF-GCN glycoproteins to block entry of NiV and HeV live virus (FIG. 8). This also indicates that mice immunized with these preparations of sF may be used to generate murine monoclonal antibodies specific for F, some of which would be expected to be cross-reactive. The results indicate that sF glycoprotein preparations are immunogenic, will elicit antibodies that can recognize native full-length F glycoproteins, will elicit cross-reactive antibodies and will elicit cross-reactive virus-neutralizing antibodies when administer as a vaccine. In addition, the data indicates that sF could be used as a diagnostic tool for the detection of anti-HeV or anti-NiV antibodies from animal and human sources.

TABLE 1

Summary of different mouse immunizations with various sF protein preparations. Balb/C mice were primed with the indicated antigen and subsequently boosted 3 times with a different S protein affinity purified sF antigen (in some cases the S-peptide tagged was removed) with 28 days intervals. Mice were bled 10 days after each boost immunization. Serum were collected and pooled.

| Mouse No. | Immunizations Primed antigen 1× | Boost antigen 3× | Cross reactive |
|---|---|---|---|
| 3 and 4 | HeV sF S tagged | HeV sF S tagged | Yes |
| 5 and 6 | HeV sF S tagged | HeV sF-GCN untagged | Yes |
| 7 and 8 | NiV sF GPI S tagged | NiV sF-GCN untagged | Yes |

TABLE 2

Serum neutralization of NiV and HeV. Serum from mouse immunized with the indicated proteins were serially diluted in a 96-well plate in EMEM and mixed with 200 TCID$_{50}$ of either HeV or NiV for 30 min at 37° C. 2 × 10$^4$ Vero cells were added to each well, incubated for 3 days at 37° C. and observed for signs of viral cytopathic effect (CPE). The serum titer was determined as the highest dilution in which viral CPE was fully neutralized.

| Mouse No. | Immunized with | Neutralization titer (Serum dilution) HeV | NiV |
|---|---|---|---|
| 5 | HeV sF GCN | 1:10 | 1:10 |
| 6 | HeV sF | 1:40 | 1:20 |
| 7 | NiV sF GCN | 1:5 | 1:160 |
| 8 | NiV sF GPI | <1:5 | 1:40 |
| control | SARS CoV | <1:5 | <1:5 |

Example 5: Sedimentation Equilibrium Experiments

Materials and Methods.

Analytical ultracentrifugation measurements were performed on a Beckman XL-A Optima analytical ultracentrifuge with an An-60 Ti rotor at 4° C. Protein samples were dialyzed overnight into PBS with 0.01% Triton X-100 buffer, loaded at initial concentrations of 0.75, 1.5 and 3 mg/ml, and analyzed at rotor speeds of 6,000 and 7,500 rpm. Data were acquired at two wavelengths per rotor speed and were fit using the program NONLIN to a single species model of the natural logarithm of the absorbance versus radial distance squared. (Johnson et. al. (1981) Biophys. J. 36(3): 575-88.) Solvent density and protein partial specific volume parameters were calculated taking into account the solvent and protein composition, respectively. (Laue et. al. (1992) Royal Society of Chemistry, Cambridge, United Kingdom.).

Results.

Figure 9:
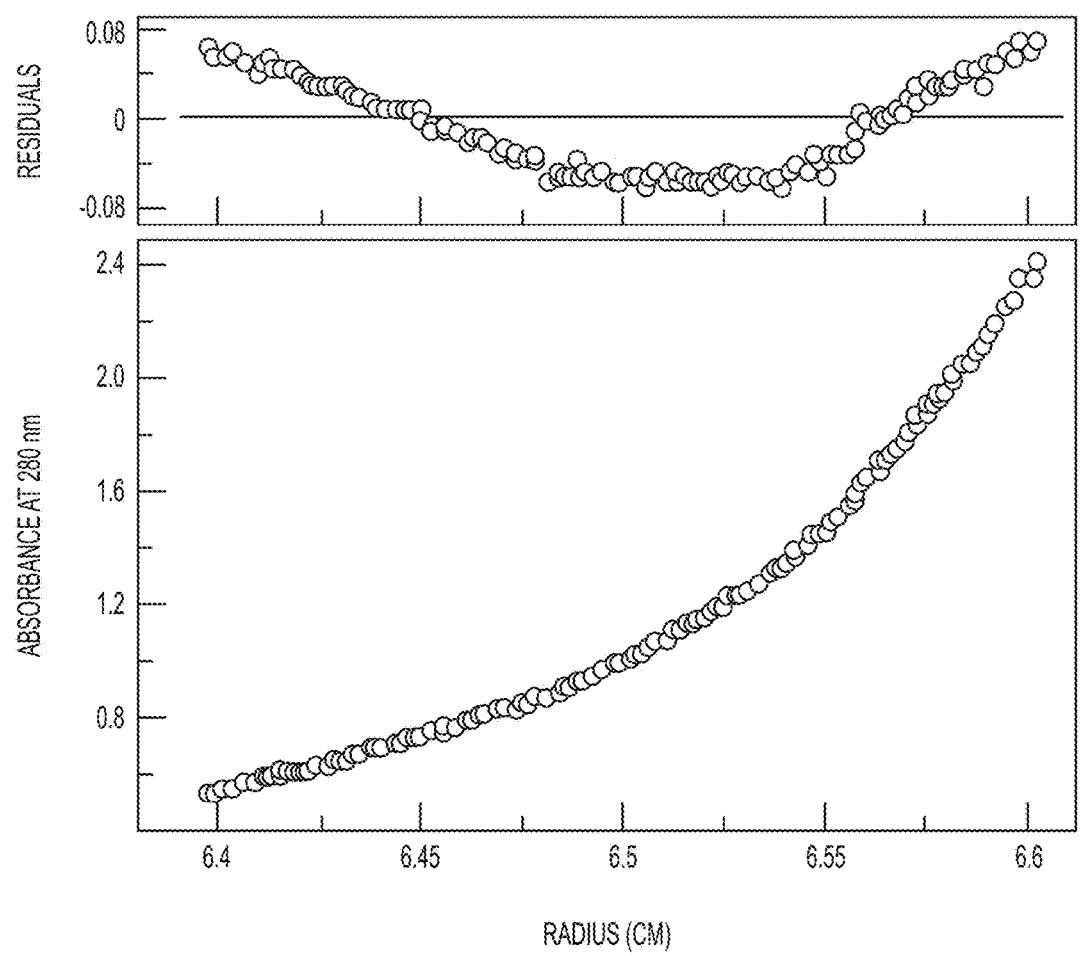
FIG. 9 shows representative equilibrium sedimentation data (6,000 rpm) of HeV sF GCN (1.5 mg/ml) in PBS with 0.01% Triton X-100 buffer at 4° C. Data are plotted as absorbance versus the radius from the axis of rotation. The data fit closely to a trimeric complex. The deviation in the data from the linear fit for a trimeric model is plotted (upper).

Sedimentation equilibrium measurements were carried out to determine the oligomeric state of the purified HeV sF GCN. The protein is trimeric, with an apparent molecular mass of ~215 kDa (FIG. 9). There was no systematic dependence of apparent molecular mass on protein concentration over a 4-fold range of protein concentration studied.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

What is claimed is:

1. A soluble polypeptide comprising a soluble antigenic form of a Nipah F glycoprotein, wherein (i) the glycoprotein consists of an amino acid sequence with at least 90 percent sequence identity to amino acids 1 to 488 of SEQ ID NO: 4, (ii) the glycoprotein is fused to a second peptide, and (iii) the second peptide is a trimerization domain which is SEQ ID NO: 10.

2. The soluble polypeptide of claim 1, wherein the glycoprotein has at least 98 percent identity to amino acids 1 to 488 of SEQ ID NO: 4.

3. The soluble polypeptide of claim 1, wherein the glycoprotein consists of amino acids 1 to 488 of SEQ ID NO: 4.

4. The soluble polypeptide of claim 1, wherein the second peptide is located in proximity to the carboxyl terminus of the glycoprotein.

5. A pharmaceutical composition comprising the soluble polypeptide of claim 1 and a pharmaceutically acceptable carrier.

6. A diagnostic kit for detecting a *Henipavirus* infection in a subject comprising the soluble polypeptide of claim 1.

* * * * *

UNITED STATES PATENT AND TRADEMARK OFFICE
CERTIFICATE OF CORRECTION

PATENT NO. : 10,040,825 B2  
APPLICATION NO. : 12/808930  
DATED : August 7, 2018  
INVENTOR(S) : Yee-peng Chan et al.

It is certified that error appears in the above-identified patent and that said Letters Patent is hereby corrected as shown below:

In the Specification

In Column 1, Lines 17-19, delete "The present invention arose in part from research funded by the following federal grants: U54 AI057168 and R21 AI065597." and add --This invention was made with government support under U54 AI057168 and R21 AI065597 awarded by the National Institutes of Health.--

In Column 1, Line 19, delete "may have" and add --has--

Signed and Sealed this  
Twenty-second Day of October, 2019

Andrei Iancu  
*Director of the United States Patent and Trademark Office*